(12) United States Patent
Kang

(10) Patent No.: US 9,855,042 B1
(45) Date of Patent: Jan. 2, 2018

(54) END EFFECTOR OF SURGICAL LINEAR STAPLER

(71) Applicant: MEDI TULIP CO., Ltd, Cheongju-si, Chungcheongbuk-do (KR)

(72) Inventor: Tae Woong Kang, Daejeon (KR)

(73) Assignee: MEDI TULIP CO., LTD, Cheongju-si, Chungcheongbuk-Do (KR)

( * ) Notice: Subject to any disclaimer, the term of this patent is extended or adjusted under 35 U.S.C. 154(b) by 0 days.

(21) Appl. No.: 15/210,890

(22) Filed: Jul. 15, 2016

(30) Foreign Application Priority Data

Jul. 8, 2016 (KR) .................. 10-2016-0087182

(51) Int. Cl.
*A61B 17/068* (2006.01)
*A61B 17/072* (2006.01)

(52) U.S. Cl.
CPC ........... *A61B 17/07207* (2013.01); *A61B 2017/07257* (2013.01); *A61B 2017/07271* (2013.01); *A61B 2017/07285* (2013.01)

(58) Field of Classification Search
CPC ........... A61B 2017/07271; A61B 2017/07278; A61B 17/07207
See application file for complete search history.

(56) References Cited

U.S. PATENT DOCUMENTS

| 5,865,361 | A | 2/1999 | Milliman et al. |
| 2012/0241498 | A1 | 9/2012 | Gonzalez et al. |
| 2013/0256383 | A1* | 10/2013 | Aronhalt ............ A61B 17/0682 227/180.1 |
| 2014/0166726 | A1* | 6/2014 | Schellin ........... A61B 17/07207 227/178.1 |
| 2015/0297223 | A1 | 10/2015 | Huitema et al. |
| 2015/0297229 | A1* | 10/2015 | Schellin ............... A61B 17/105 227/177.1 |

FOREIGN PATENT DOCUMENTS

| EP | 2932912 A1 | 10/2015 |
| JP | 2015-107222 A | 6/2015 |
| JP | 2016-509525 A | 3/2016 |
| KR | 10-2015-0126622 A | 11/2015 |
| WO | 2016/044216 A1 | 3/2016 |

* cited by examiner

*Primary Examiner* — Andrew M Tecco
(74) *Attorney, Agent, or Firm* — Revolution IP, PLLC

(57) ABSTRACT

Disclosed is an end effector of a surgical linear stapler, which includes a staple cartridge, an anvil, a pusher unit, a driving wedge, a stabilizer unit and a blade unit, wherein the stabilizer unit is arranged on the staple cartridge while neighboring on the pusher unit and at least partially discharged from the staple cartridge by the driving wedge so as to hold tissue placed in between the staple cartridge and the anvil.

19 Claims, 28 Drawing Sheets

[Fig. 1]
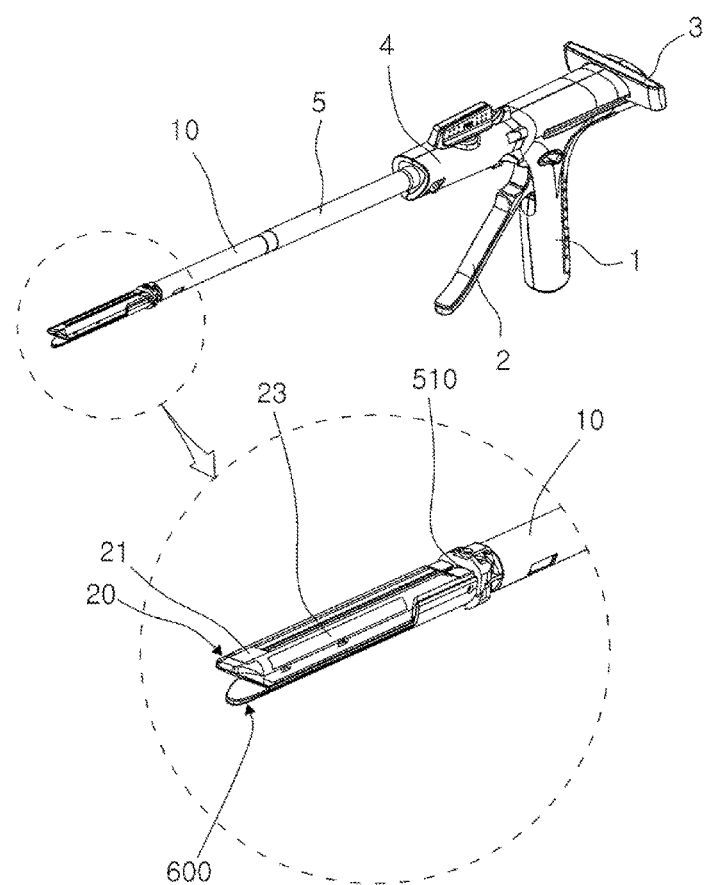

[Fig. 2]
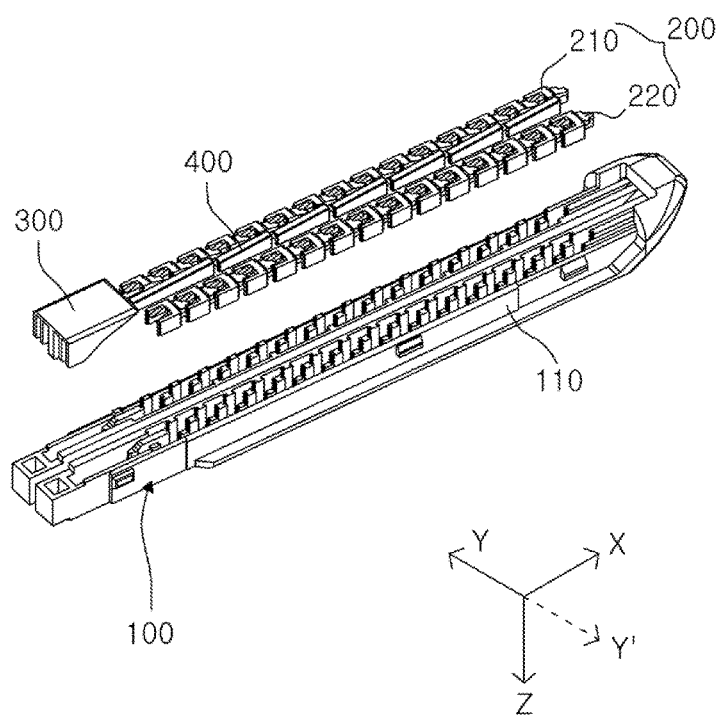

[Fig. 3]
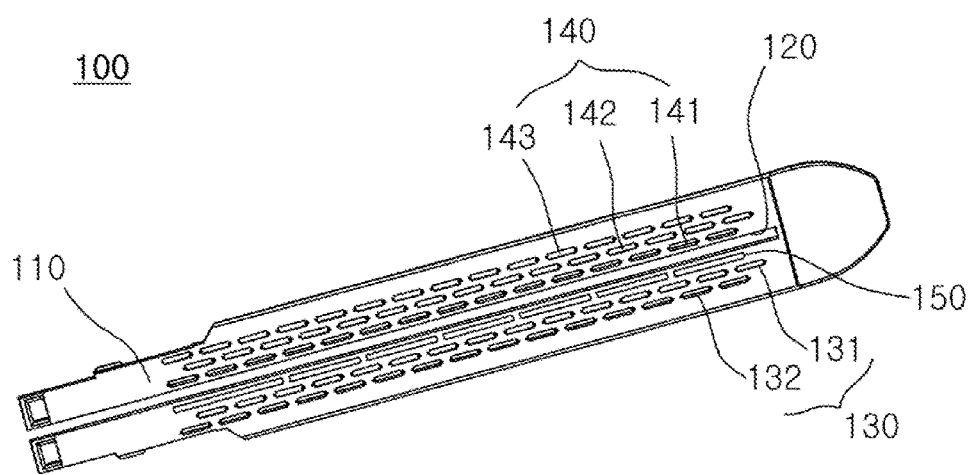

[Fig. 4]
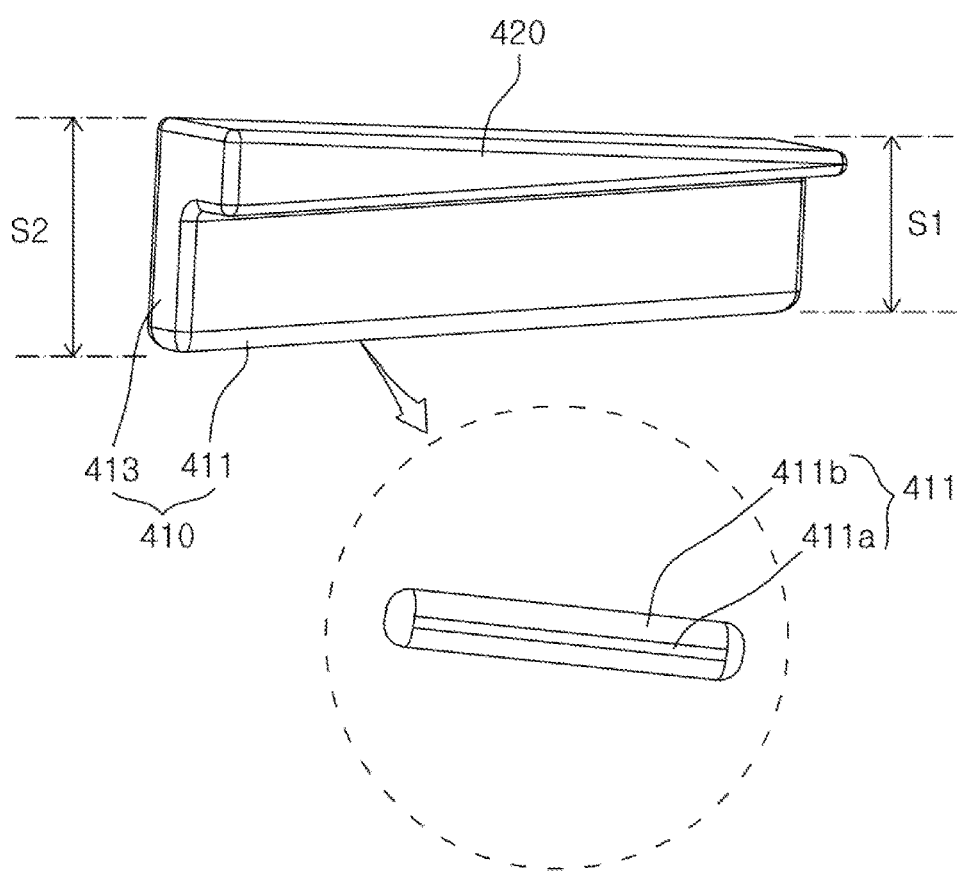

【Fig. 5】
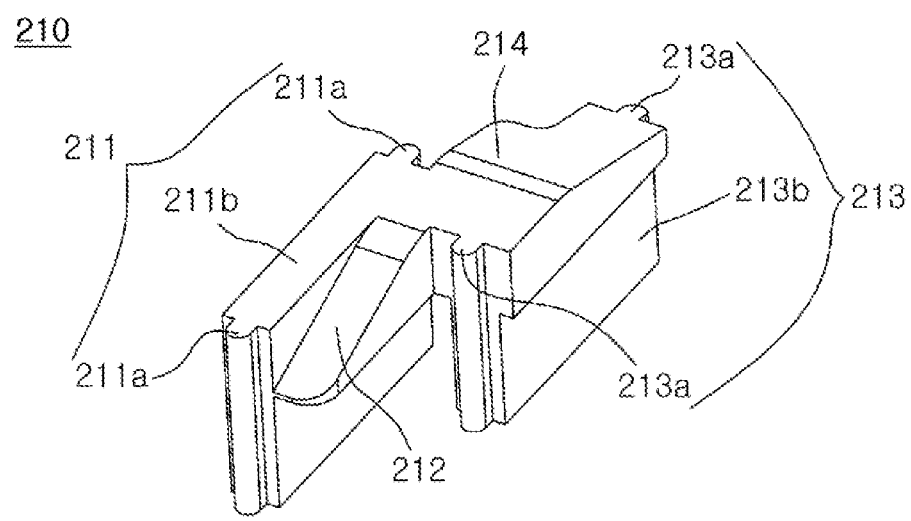
(a)
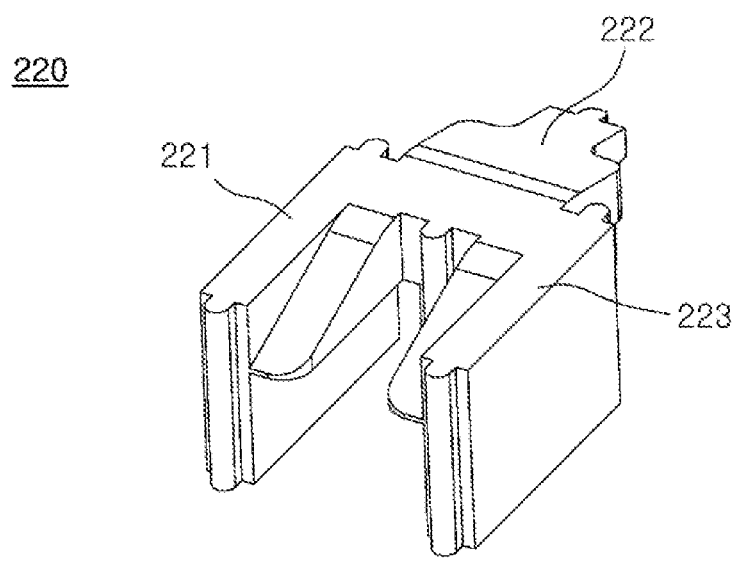
(b)

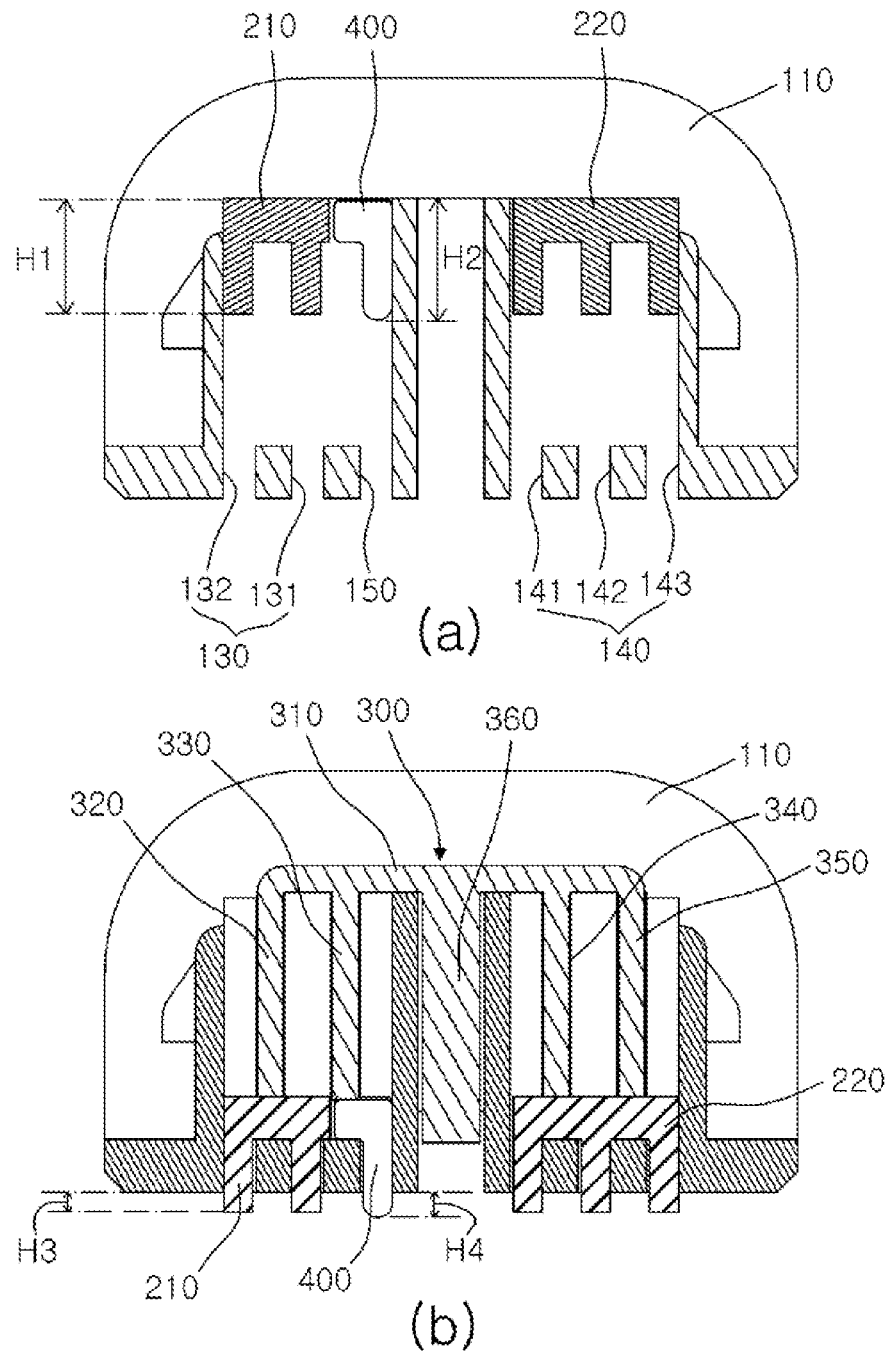
[Fig. 6]

[Fig. 7]
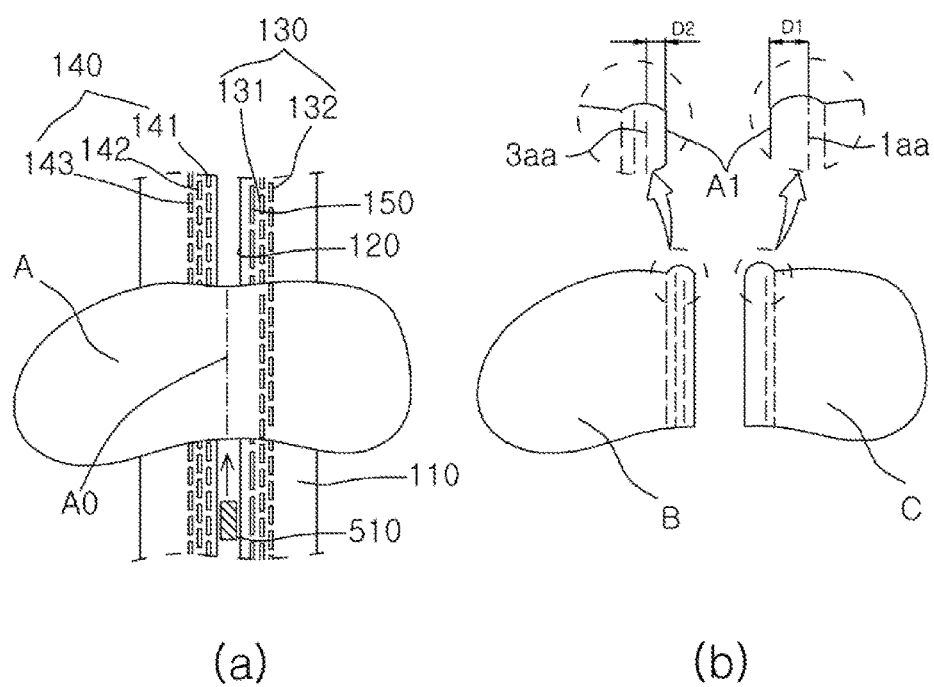
(a)  (b)

[Fig. 8]
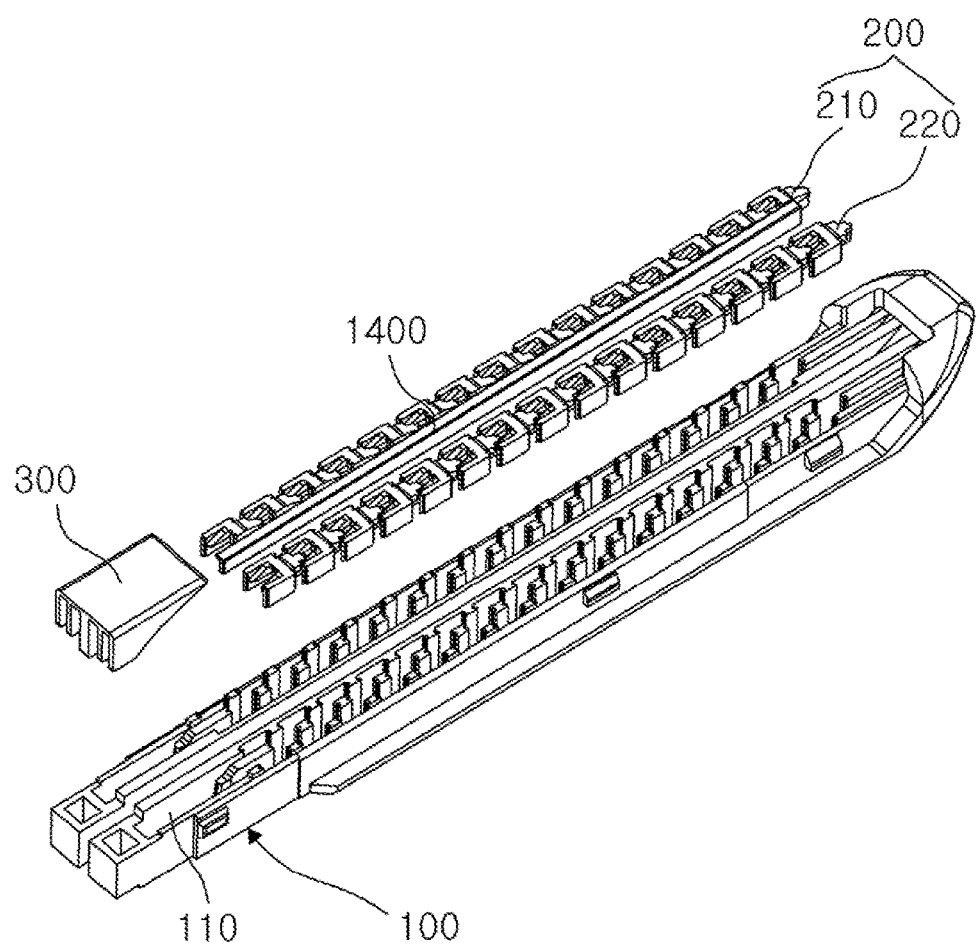

[Fig. 9]
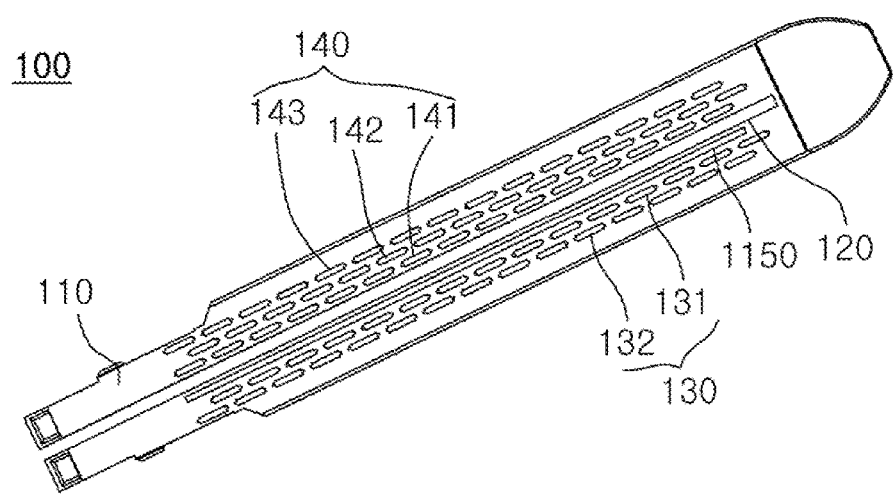

[Fig. 10]
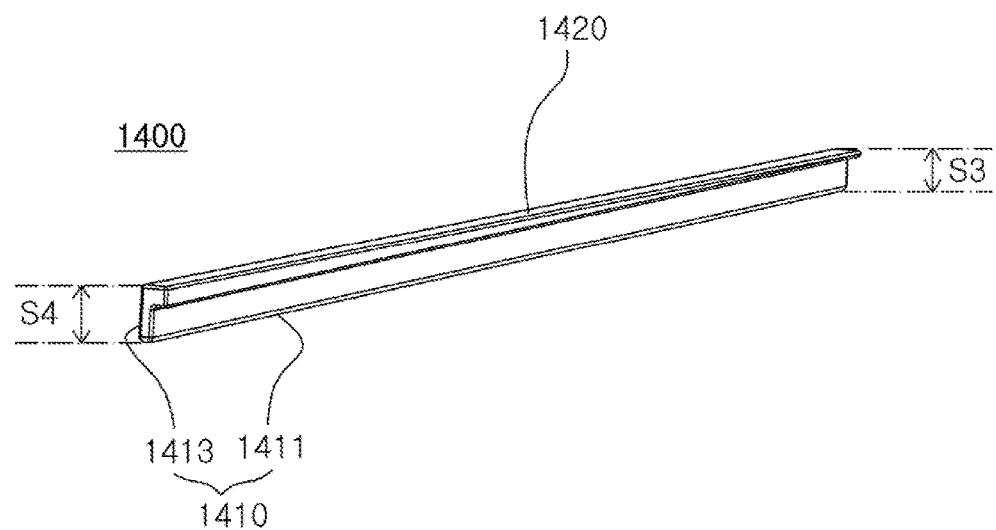

【Fig. 11】
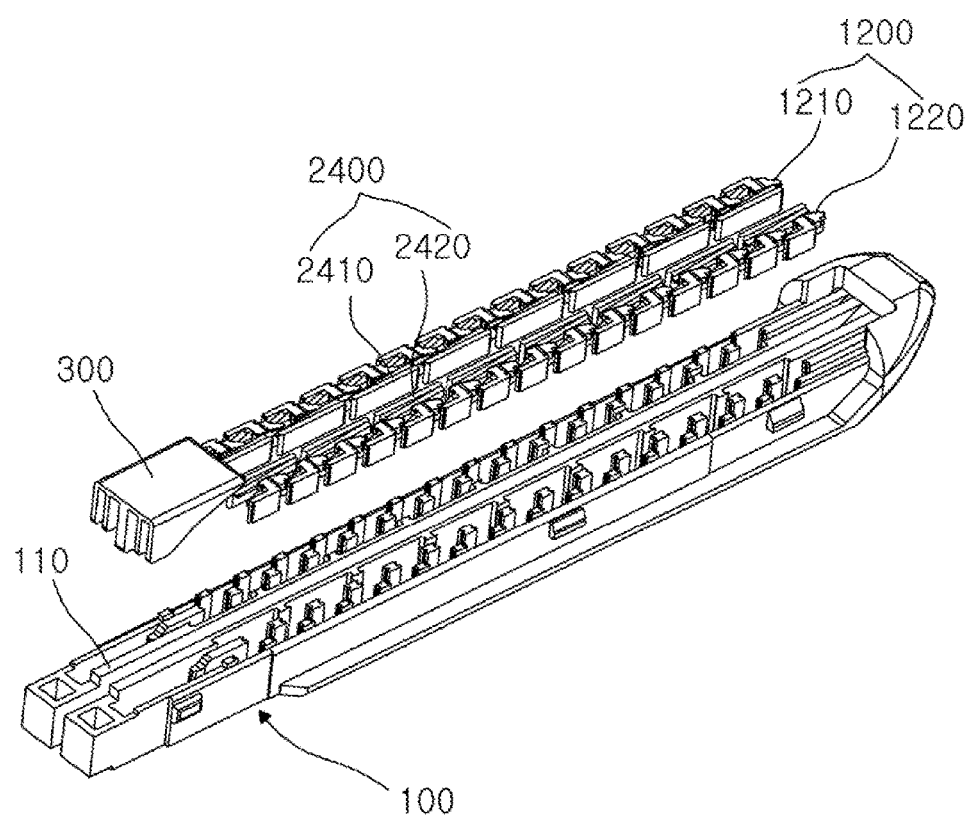

[Fig.12]
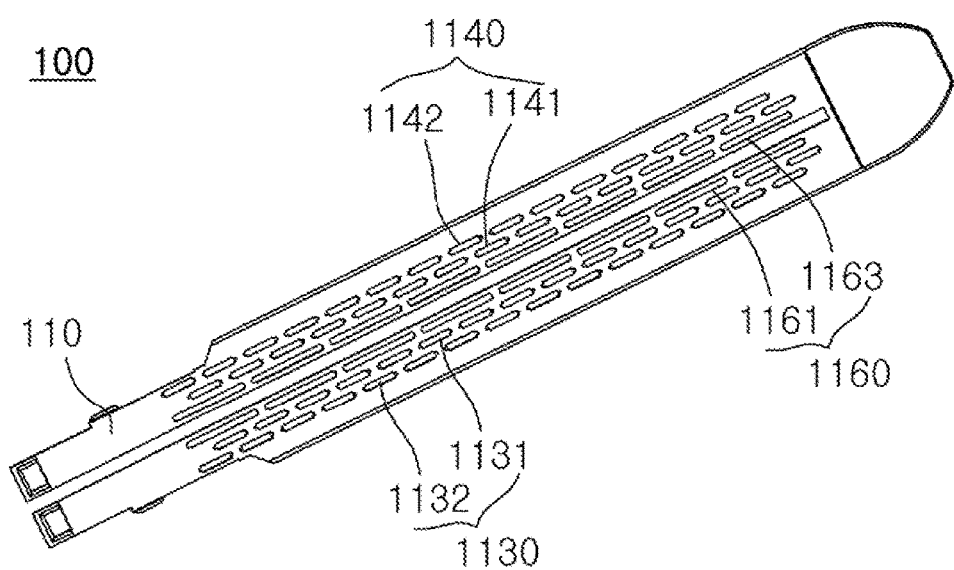

【Fig. 13】
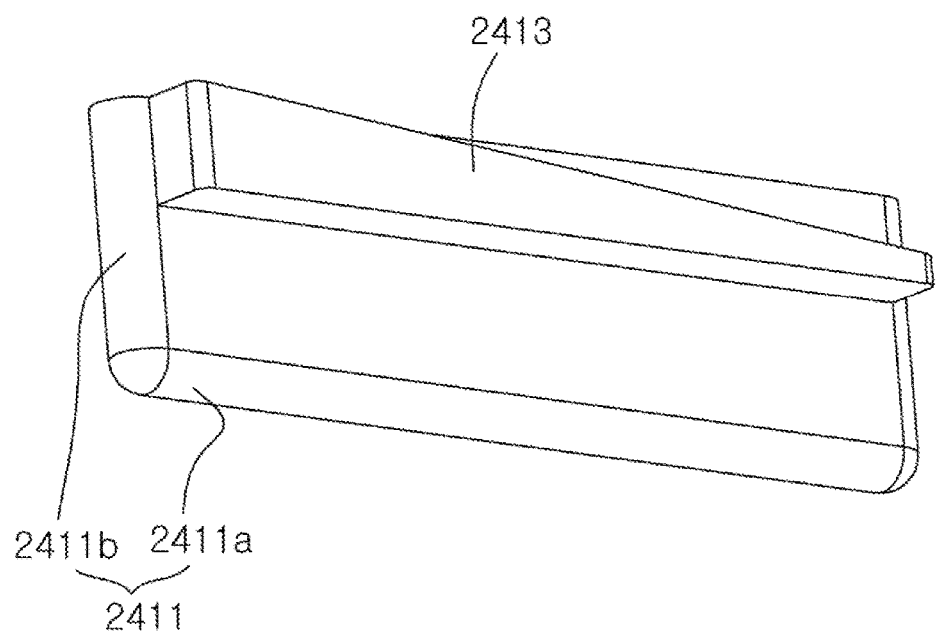

【Fig. 14】
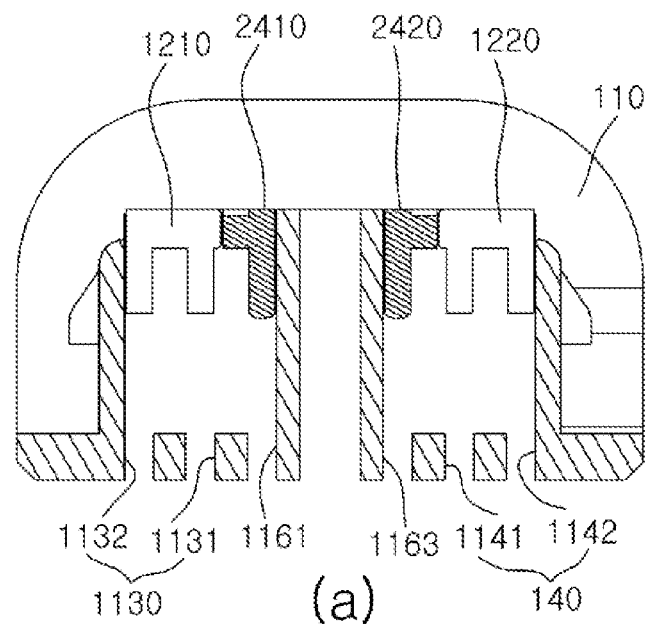
(a)
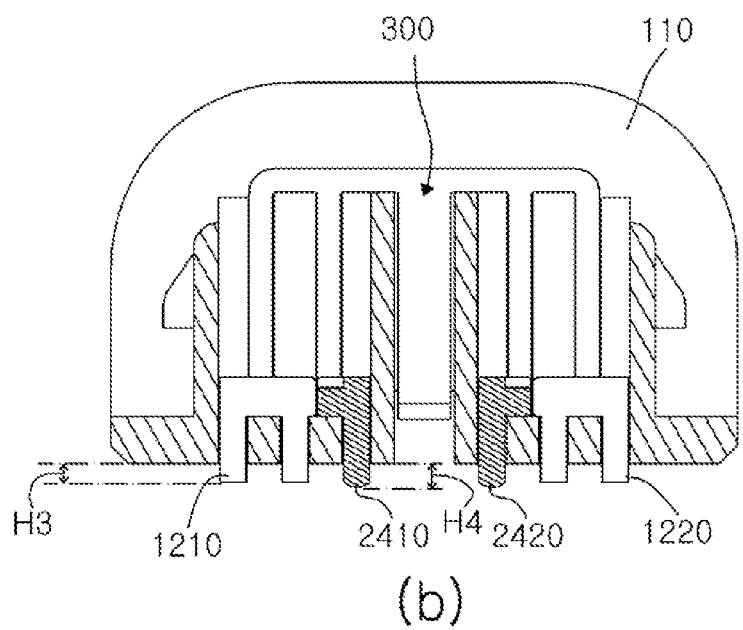
(b)

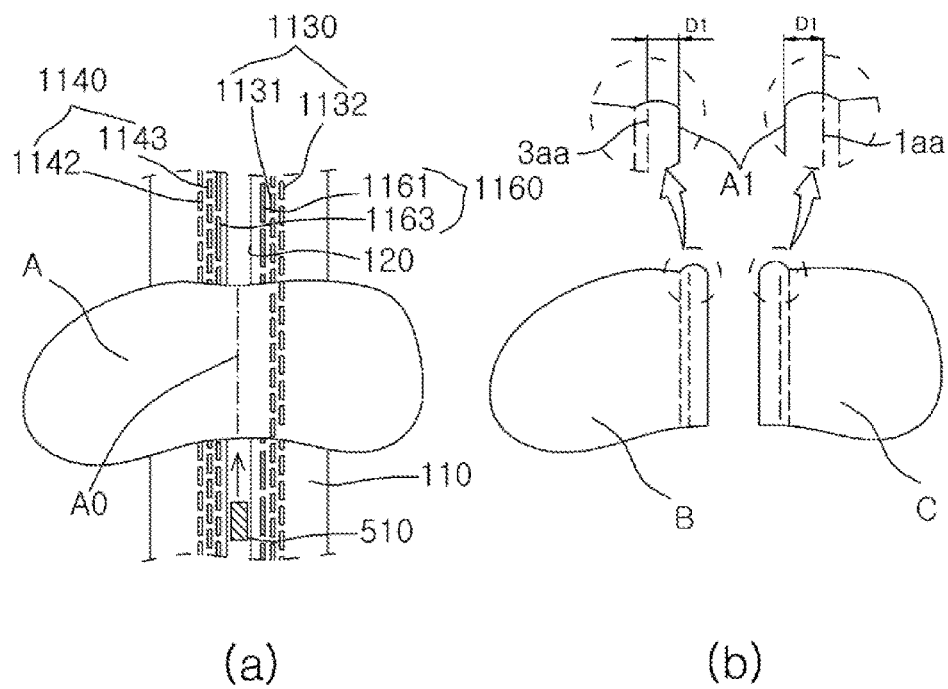
[Fig. 15]

[Fig. 16]
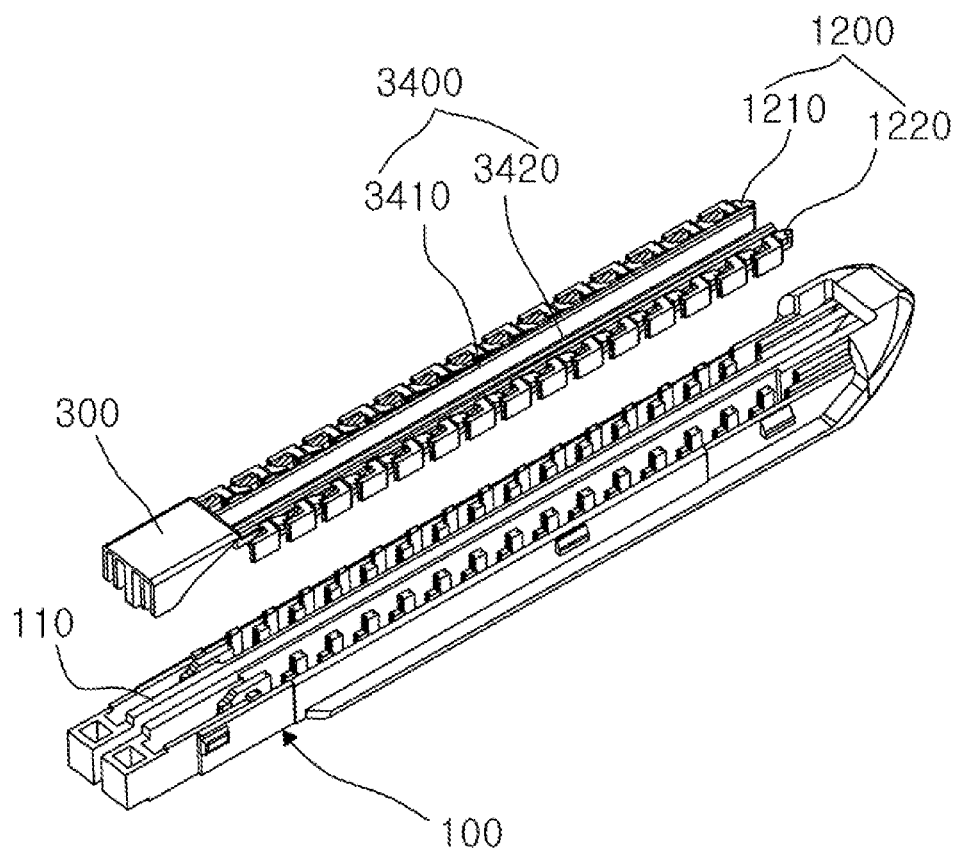

[Fig. 17]
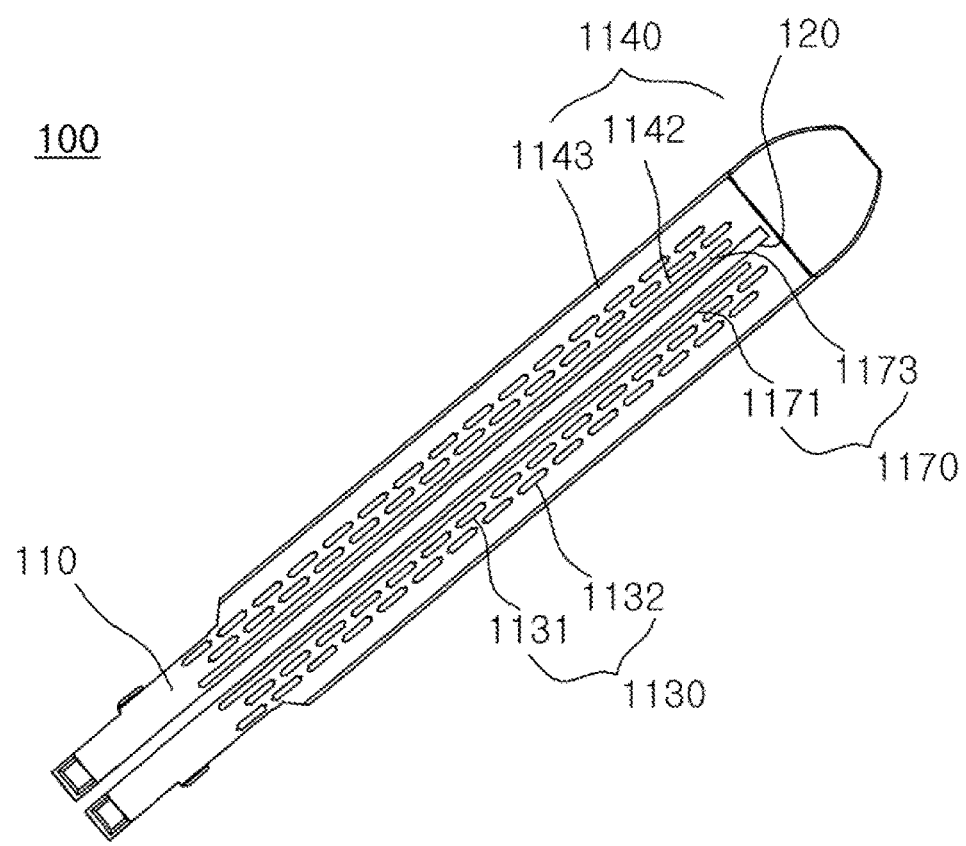

【Fig. 18】
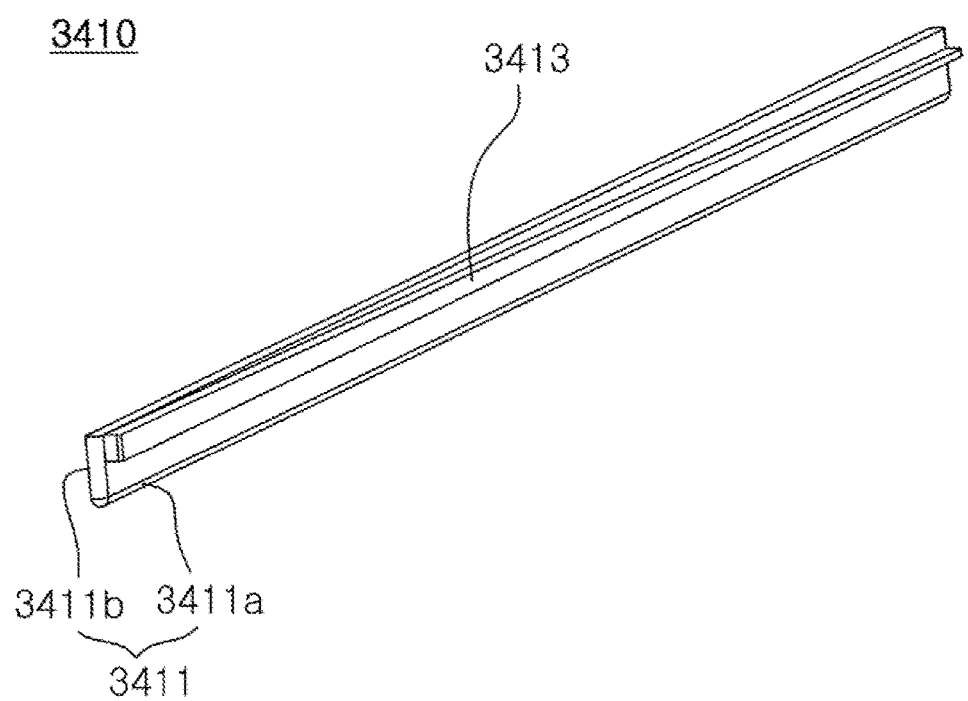

[Fig. 19]
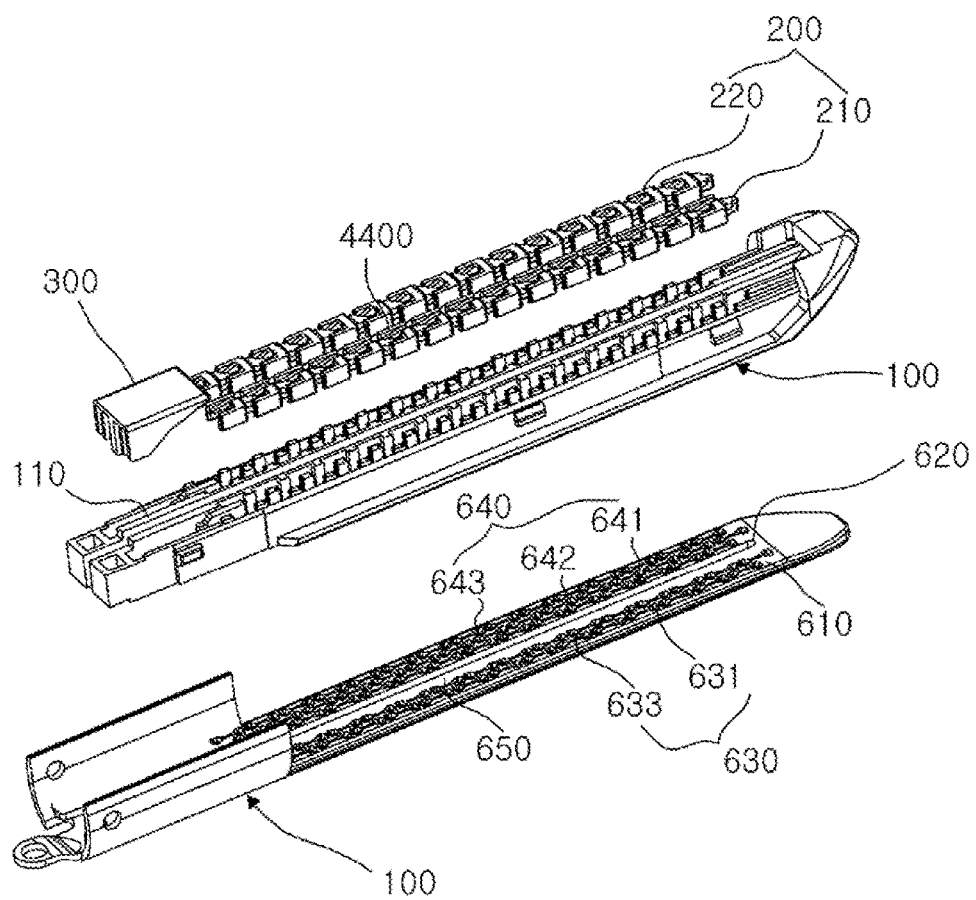

[Fig. 20]
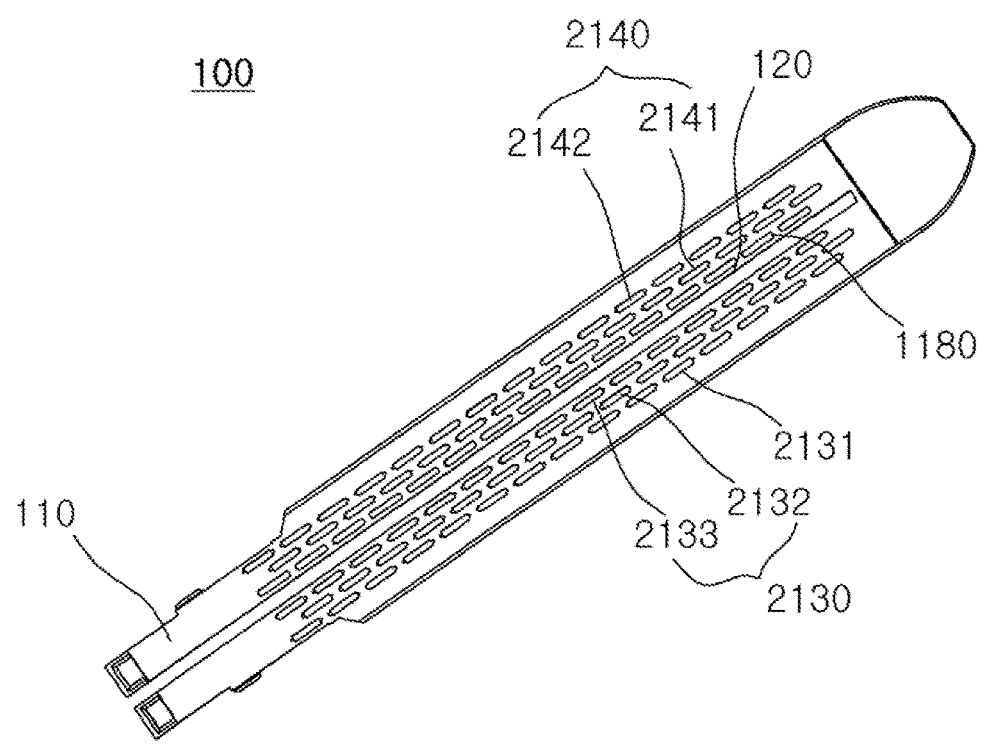

[Fig. 21]
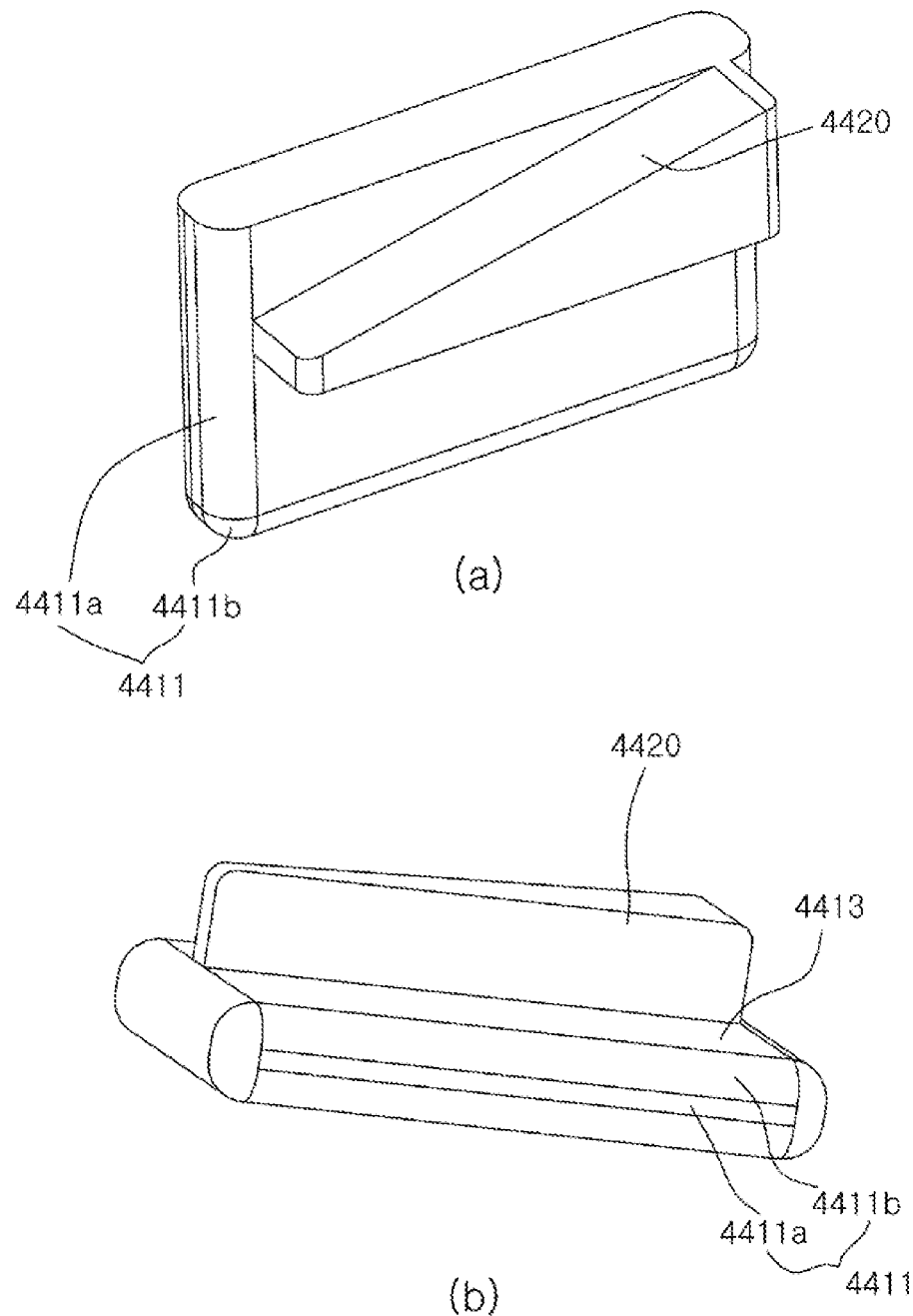

[Fig. 22]
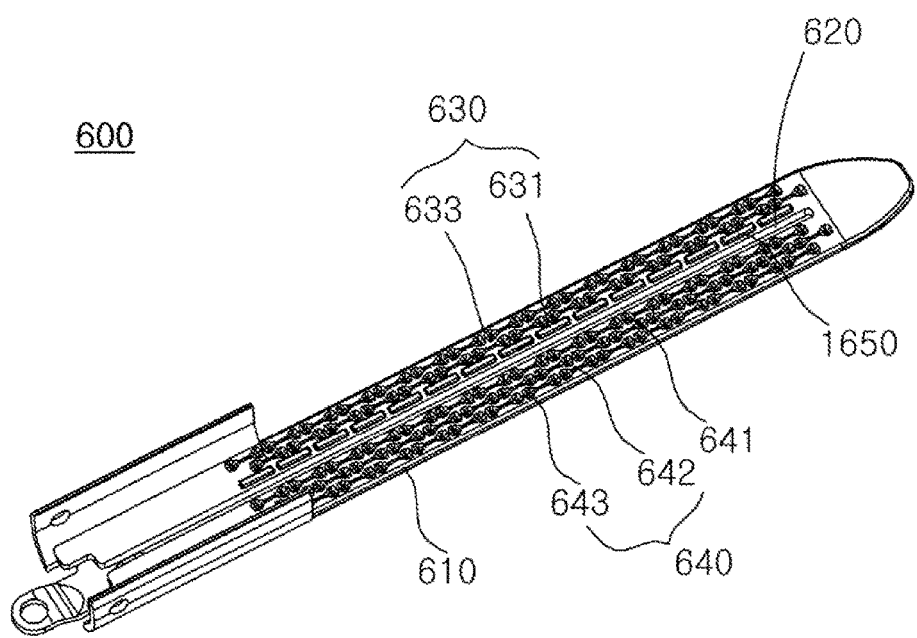

[Fig. 23]
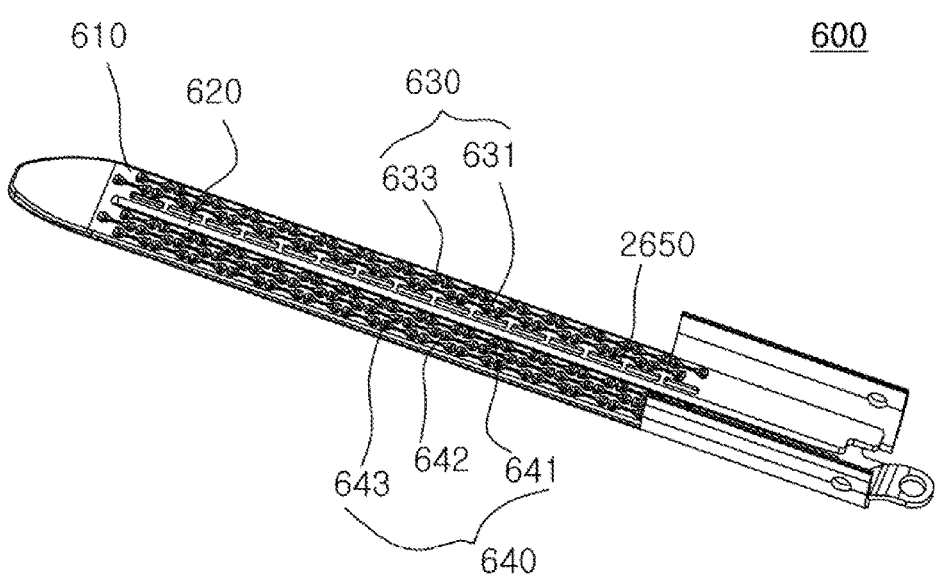

[Fig. 24]
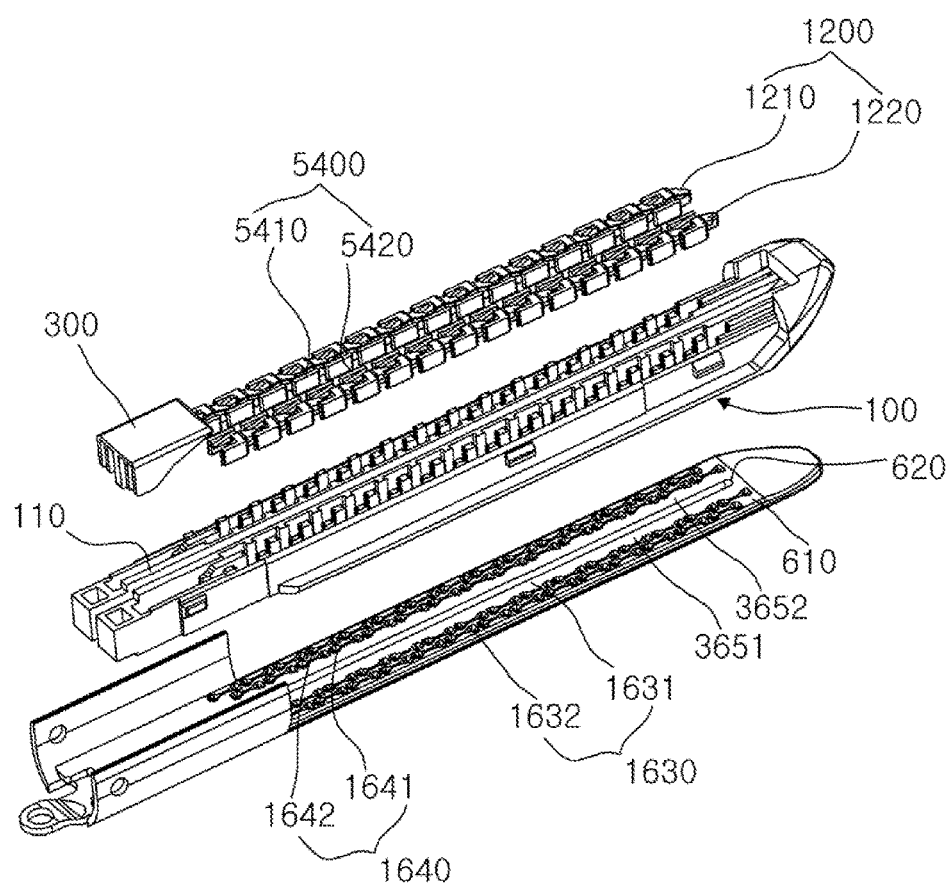

[Fig. 25]
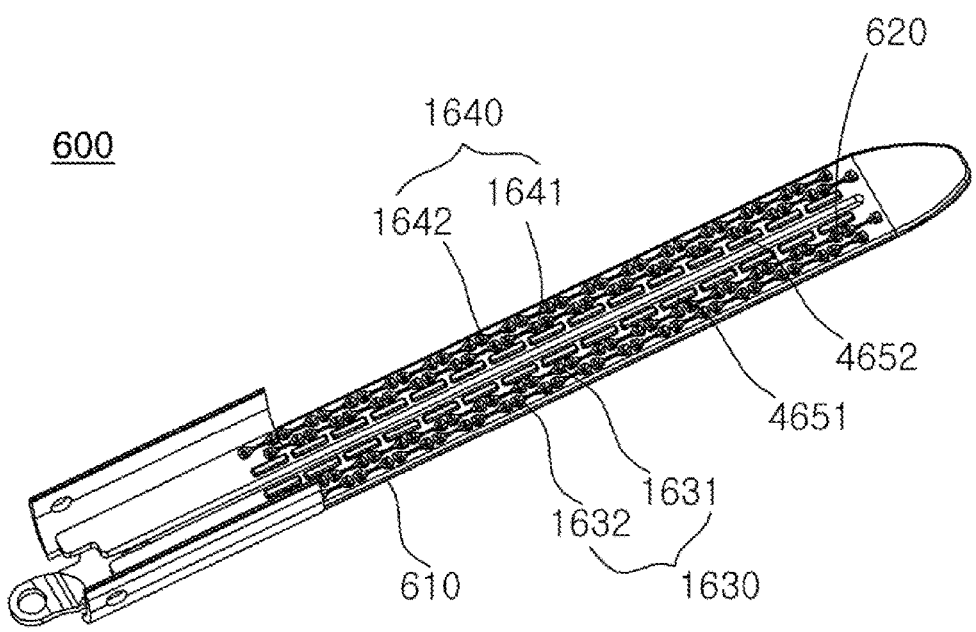

[Fig. 26]
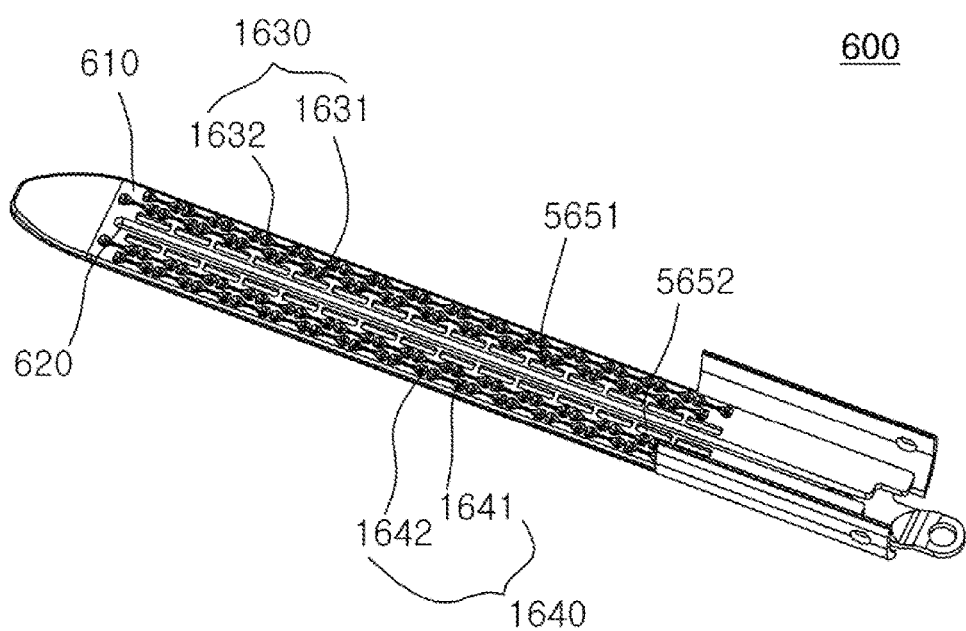

[Fig. 27]
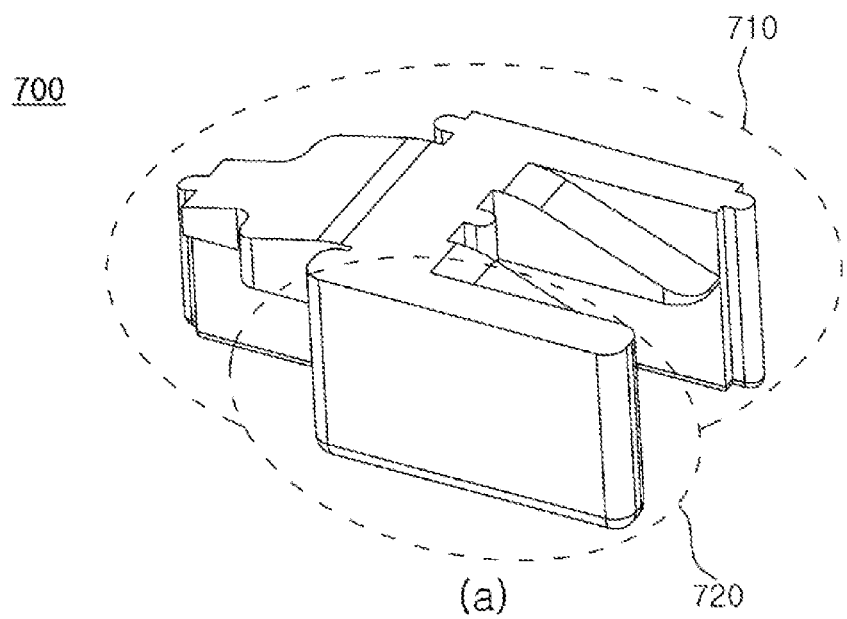
(a)
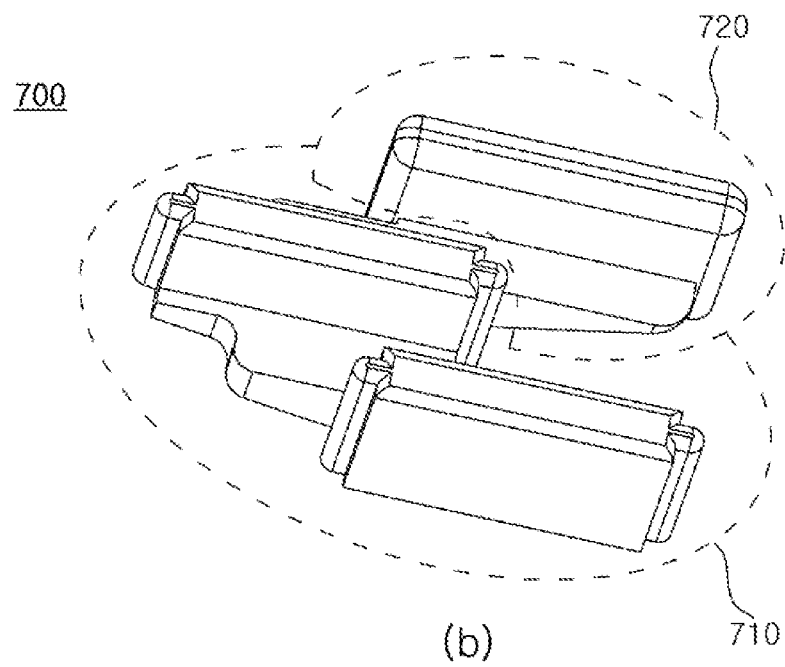
(b)

【Fig. 28】
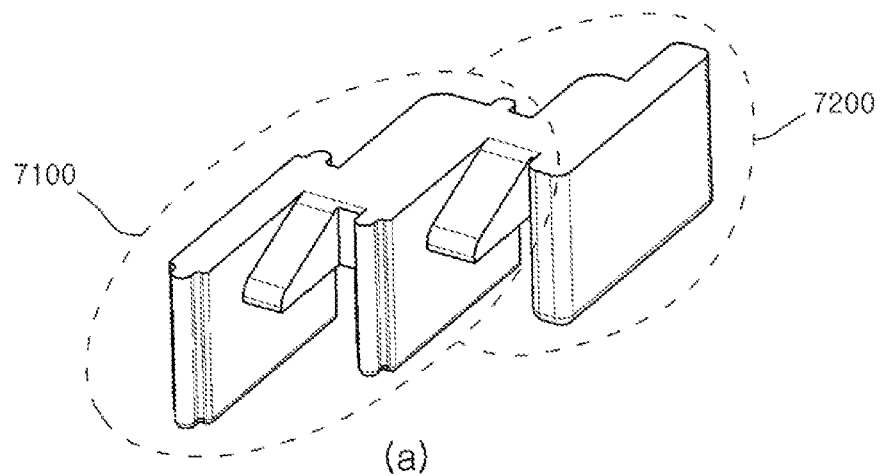
(a)
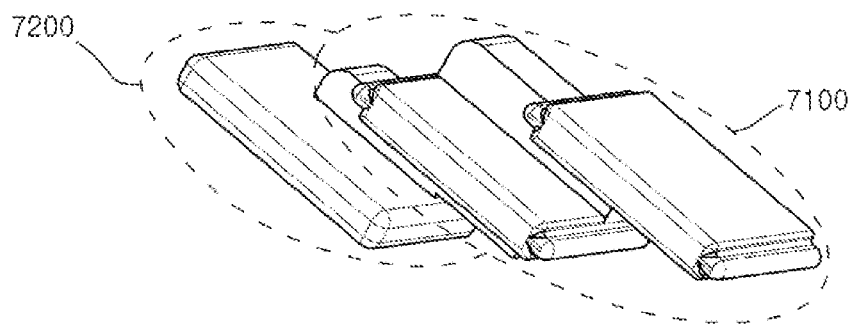
(b)

END EFFECTOR OF SURGICAL LINEAR STAPLER

CROSS-REFERENCE TO RELATED APPLICATION

This application claims priority from Korean Patent Application No. 10-2016-0087182, filed on Jul. 8, 2016 in the Korean Intellectual Property Office, the disclosure of which is incorporated herein by reference.

BACKGROUND OF THE INVENTION (a) Field of the Invention

The present invention relates to an end effector of a surgical linear stapler, and more particularly to an end effector of a surgical linear stapler which can stably and conveniently obtain tissue for pathological examination, which is not damaged by a staple, while stapling and cutting a surgical site.

(b) Description of the Related Art

In general, a surgical stapler is a medical instrument mainly used for cutting and anastomosis of an organ in abdominal and thoracic surgery. Such a surgical stapler is classified into an open stapler used in thoracotomy and laparotomy and an endo stapler used in thoracoscopic surgery and celioscopic surgery.

The surgical stapler has advantages of not only shortening operation time since cutting of a surgical site and anastomosis of an organ are performed at a time, but also accurately stapling the surgical site. Besides, the surgical stapler has advantages of a quicker recovery and a smaller scar than those of when tissue is cut and stapled using a surgical stapling thread, and has been thus widespread in the modern surgical operation. In particular, the surgical stapler has been widely used for cutting cancer tissue and stapling a cut site in cancer surgery.

However, biological tissue adjacent to a section obtained for frozen section tissue examination from a surgical site removed after being stapled and cut by a conventional stapler is damaged by a staple, and it is therefore difficult to correctly examine whether a cancer cell is remained in a cutting margin.

SUMMARY OF THE INVENTION

Accordingly, the present invention is conceived to solve the foregoing problems, and an aspect of the present invention is to provide an end effector of a surgical linear stapler capable of stably and conveniently obtaining tissue for pathological examination, which is not damaged by a staple, while stapling and cutting a surgical site.

In accordance with an embodiment of the present invention, there is provided an end effector of a surgical linear stapler, including: a staple cartridge which is internally loaded with staples for stapling tissue; an anvil which corresponds to the staple cartridge and forms the staple discharged from the staple cartridge; a pusher unit which is arranged on the staple cartridge while corresponding to the staple and pushes the staple in a height direction of the staple cartridge, i.e. a first direction while being moved by external force so that the staple can be discharged from the staple cartridge; a driving wedge which is arranged on the staple cartridge and presses the pusher unit in the first direction while being moving along a lengthwise direction of the staple cartridge, i.e. a second direction by external force; a stabilizer unit which is arranged on the staple cartridge while neighboring on the pusher unit and at least partially discharged from the staple cartridge by the driving wedge to hold tissue placed in between the staple cartridge and the anvil; and a blade unit which includes a blade for cutting tissue stapled by the staples and moves the driving wedge in the second direction.

BRIEF DESCRIPTION OF THE DRAWINGS

The above and/or other aspects of the present invention will become apparent and more readily appreciated from the following description of the exemplary embodiments, taken in conjunction with the accompanying drawings, in which:

FIG. 1 illustrates a surgical linear stapler according to a first embodiment of the present invention;

FIG. 2 illustrates a part of an end effector of the surgical linear stapler in FIG. 1;

FIG. 3 illustrates a cartridge main body provided in the end effect of the surgical linear stapler in FIG. 2;

FIG. 4 illustrates a unit stabilizer provided in the end effector of the surgical linear stapler in FIG. 2;

FIG. 5 illustrates a first pusher and a second pusher provided in the end effector of the surgical linear stapler in FIG. 2;

FIG. 6 illustrates states before and after a pusher unit and a stabilizer unit are pressed by a driving wedge in the end effector of the surgical linear stapler in FIG. 2;

FIG. 7 illustrates states before stapling tissue and after cutting tissue by the surgical linear stapler of FIG. 1;

FIG. 8 illustrates a part of an end effector of a surgical linear stapler according to a second embodiment of the present invention;

FIG. 9 illustrates a cartridge main body provided in the end effector of the surgical linear stapler in FIG. 8;

FIG. 10 illustrates a stabilizer unit provided in the end effector of the surgical linear stapler in FIG. 8;

FIG. 11 illustrates a part of an end effector of a surgical linear stapler according to a third embodiment of the present invention;

FIG. 12 illustrates a cartridge main body provided in the end effector of the surgical linear stapler in FIG. 11;

FIG. 13 illustrates a unit stabilizer provided in the end effector of the surgical linear stapler in FIG. 11;

FIG. 14 illustrates states before and after a pusher unit and a stabilizer unit are pressed by a driving wedge in the end effector of the surgical linear stapler in FIG. 11;

FIG. 15 illustrates states before stapling tissue and after cutting tissue by the end effector of the surgical linear stapler in FIG. 11;

FIG. 16 illustrates a part of an end effector of a surgical linear stapler according to a fourth embodiment of the present invention;

FIG. 17 illustrates a cartridge main body provided in the end effector of the surgical linear stapler in FIG. 16;

FIG. 18 illustrates a stabilizer unit provided in the end effector of the surgical linear stapler in FIG. 11;

FIG. 19 illustrates a part of an end effector of a surgical linear stapler according to a fifth embodiment of the present invention;

FIG. 20 illustrates a cartridge main body provided in the end effector of the surgical linear stapler in FIG. 19;

FIG. 21 illustrates a unit stabilizer provided in the end effector of the surgical linear stapler in FIG. 19;

FIG. 22 illustrates an anvil provided in an end effector of a surgical linear stapler according to a sixth embodiment of the present invention;

FIG. 23 illustrates an anvil provided in an end effector of a surgical linear stapler according to a seventh embodiment of the present invention;

FIG. 24 illustrates a part of an end effector of a surgical linear stapler according to an eighth embodiment of the present invention;

FIG. 25 illustrates an anvil provided in an end effector of a surgical linear stapler according to a ninth embodiment of the present invention;

FIG. 26 illustrates an anvil provided in an end effector of a surgical linear stapler according to a tenth embodiment of the present invention;

FIG. 27 illustrates an embodiment of a pusher-stabilizer unit that can replace both the stabilizer unit and the pusher unit used in the end effector of the surgical linear stapler in FIG. 24 according to the eighth embodiment; and FIG. 28 illustrates another embodiment of a pusher-stabilizer unit that can replace both the stabilizer unit and the pusher unit used in the end effector of the surgical linear stapler in FIG. 24 according to the eighth embodiment.

DETAILED DESCRIPTION OF THE EMBODIMENTS

Hereinafter, exemplary embodiments of the present invention for solving the foregoing problems will be described with reference to accompanying drawings. Throughout the following exemplary embodiments, like numerals refer to like elements and repetitive descriptions will be avoided as necessary.

A surgical linear stapler and an end effector for the same according to a first embodiment of the present invention for obtaining tissue for pathological examination will be described with reference to FIG. 1 to FIG. 7.

Referring to FIG. 1, the surgical linear stapler includes a handle assembly, an extension shaft 5 and an end effector.

The handle assembly includes a support grip 1, a control grip 2, a pull grip 3, a rotary head 4, and a control bar (not shown).

The control bar is interlocked with the control grip 2 while penetrating the extension shaft 5 and the rotary head 4 and also connects with the pull grip 3.

The control bar moves forward when the control grip 2 is manipulated, and moves backward when a user pulls the pull grip 3 backward.

The rotary head 4 is provided in a front area of the handle assembly and makes the extension shaft 5 and the end effector be rotated 360° in the front area of the handle assembly while inserting the control bar therein.

The extension shaft 5 is placed in between the end effector and the rotary head 4, and a part of the control bar is arranged inside the extension shaft 5.

Referring to FIG. 1 to FIG. 7, the end effector of the surgical linear stapler includes a stapling shaft 10, a staple cartridge assembly 20, an anvil 600, a pusher unit 200, a driving wedge 300, a stabilizer unit 400 and a blade unit with a blade 510.

The staple cartridge assembly 20 includes a staple cartridge 100, an upper cover 21 placed over the staple cartridge 100, and an indicator 23 provided on the upper cover 21. The staple cartridge 100 is internally loaded with staples for stapling tissue A.

The anvil 600 corresponds to the staple cartridge 100 and forms the staple discharged from the staple cartridge 100.

The pusher unit 200 is arranged on the staple cartridge 100 while corresponding to the staples, and pushes the staple in a height direction of the staple cartridge 100, i.e. a first direction Z while moving by external force, thereby making the staples be discharged from the staple cartridge 100.

The driving wedge 300 is arranged on the staple cartridge 100 and moves a lengthwise direction of the staple cartridge 100, i.e. a second direction X by external force, thereby pressing the pusher unit 200 in the first direction Z.

The stabilizer unit 400 is arranged on the staple cartridge 100 and adjacent to the pusher unit 200. The stabilizer unit 400 is at least partially discharged from the staple cartridge 100 by the driving wedge 300 and holds tissue positioned in between the staple cartridge 100 and the anvil 600.

The blade unit includes the blade 510 for cutting the tissue stapled by the staples, and moves the driving wedge 300 along the second direction X.

Specifically, referring to FIG. 3 and FIG. 7, the staple cartridge 100 includes a cartridge main body 110, and the cartridge main body 110 is formed with a first guide slit 120, a first staple discharge hole array 130, a second staple discharge hole array 140 and a stabilizer discharge slit 150.

The first guide slit 120 is formed in a center region of the cartridge main body 110 along the lengthwise direction of the staple cartridge 100, i.e. the second direction X and guides the blade 510 to move.

The stabilizer discharge slit 150 is formed in between the first staple discharge hole array 130 and the first guide slit 120 and serves as a passage through which the stabilizer unit 400 is at least partially discharged.

The stabilizer discharge slit 150 includes a plurality of unit discharge slits formed at regular intervals along the second direction X, in which the length of the unit discharge slit in the second direction X is longer than the length of the first unit staple discharge hole in the second direction X.

Of course, the present invention is not limited to the foregoing. Alternatively, the stabilizer discharge slit 150 may be different in width from the first unit staple discharge hole.

The first staple discharge hole array 130 and the second staple discharge hole array 140 are arranged at opposite sides with respect to the first guide slit 120. The first staple discharge hole array 130 is arranged neighboring on the stabilizer discharge slit 150.

The first staple discharge hole array 130 includes a plurality of first staple discharge hole lines arranged at regular intervals along a widthwise direction of the staple cartridge 100, i.e. a third direction Y with respect to the first guide slit 120.

Specifically, the first staple discharge hole array 130 includes a 1-1 staple discharge hole line 131 the most adjacent to the first guide slit 120, and a 1-2 staple discharge hole line 132 spaced apart at a predetermined distance from the 1-1 staple discharge hole line 131 in the third direction Y.

The 1-1 staple discharge hole line 131 includes a plurality of first unit staple discharge holes formed in a row on the cartridge main body 110 at regular intervals along the second direction X.

Further, the second staple discharge hole array 140 includes a 2-1 staple discharge hole line 141 the most adjacent to the first guide slit 120, a 2-2 staple discharge hole line 142 spaced apart at a predetermined distance from the 2-1 staple discharge hole line 141 in an opposite direction to the third direction Y, i.e. a fourth direction Y', and a 2-3 staple discharge hole line 143 spaced apart at a predetermined distance from the 2-2 staple discharge hole line 142 in the fourth direction.

A first distance between the 1-1 staple discharge hole line 131 and the first guide slit 120 is greater than a second distance between the 2-1 staple discharge hole line 141 and the first guide slit 120.

The staples loaded into the 1-1 staple discharge hole line 131 are discharged out by the pusher unit 200 and formed by the anvil 600, thereby forming a first stapling line 1aa on tissue. Likewise, staples loaded into the 2-1 staple discharge hole line 141 form a second stapling line 3aa.

Therefore, a distance D1 from the cutting section A1, in which tissue A is cut, to the first stapling line 1aa is greater than a distance D2 from the cutting section A1 to the second stapling line 3aa.

In result, the tissue placed in between the cutting section A1 and the first stapling line 1aa is not damaged by the staples, and it is thus possible to obtain a tissue area for pathological examination, which is not damaged by the staples, from the tissue removed by the blade 510.

Specifically, as shown in (a) of FIG. 7, a surgical site A of tissue arranged on the cartridge main body 110 is cut by the blade 510 into two surgical sites with respect to a virtual cutting line A0. One of the two surgical sites is a first surgical site C to be removed, and the other one is a second surgical site B to be remained in a human body.

If the end effector of the surgical linear stapler according to this embodiment starts operating, as show in (b) of FIG. 7 the first surgical site C has stapling lines of two rows parallel with a cutting section A1, and the second surgical site B has stapling lines of three rows parallel with the cutting section A1.

Here, the distance D1 between the first stapling line 1aa, which is the nearest to the cutting section A1, of the stapling lines in the first surgical site C and the cutting section A1 is greater than the distance D2 between a second stapling line 3aa, which is the nearest to the cutting section A1, of the stapling lines in the second surgical site B and the cutting section A1.

Thus, biological tissue placed in between the cutting section A1 and the first stapling line 1aa in the first surgical site C is suitable for the tissue for pathological examination since it is not damaged at all.

In result, the distance from the cutting section to the stapling line of an organ site to be removed while cutting one organ into two areas and stapling them is set to be greater than the distance from the cutting section to the stapling line of the surgical site to be remained in a human body, thereby preventing a cutting margin of biological tissue for examination from being damaged in the surgical site to be removed. Therefore, it is possible to stably and conveniently obtain a tissue area for pathological examination, which is not damaged by a staple, in a surgical site of an organ to be removed.

In particular, when the staple cartridge 100 and the anvil 600 relatively move to staple the tissue, the stabilizer unit 400 is discharged from the staple cartridge 100 and holds the tissue between the cutting section A1 of the tissue and the first stapling line 1aa, so that the blade 510 can stably cut the tissue in the state that the tissue is not torn.

Referring to FIG. 1 to FIG. 3, the indicator 23 indicates a position where the stabilizer unit 400 is arranged with respect to the first guide slit 120 on the staple cartridge 100. Here, the tissue placed in between the stabilizer unit 400 and the anvil 600 is not damaged since it is not stapled by the staples.

In result, the indicator 23 indicates where the tissue having a tissue area for pathological examination, which is not damaged while the tissue is cut by the blade 510, i.e. the tissue to be removed from a human body is positioned, and thus prevents a mistake in surgery.

The indicator 23 may be provided on an outer surface of the upper cover 21 in the form of painting with certain color, a colored tape distinctive from a view of the exterior, a projection or groove having a certain shape, etc. Alternatively, the indicator 23 may be made of a material with a fluorescent substance, or a lighting unit such as a light emitting diode (LED).

Referring to FIG. 2, FIG. 4 and FIG. 6, the stabilizer unit 400 includes a plurality of unit stabilizers arranged at regular intervals along the second direction X.

Specifically, the stabilizer unit 400, i.e. the unit stabilizer includes a contact member 410 to be in contact with tissue, and a press member 420 extended from one side of the contact member 410 and pressed by the driving wedge 300.

The contact member 410 includes an upper body 413 extended from the press member 420, and a lower body 411 extended from the upper body and discharged from the staple cartridge 100 to directly contact the tissue.

The lower body 411 has a rounded surface 411b gently formed toward a bottom center region 411a of the lower body 411 in order to prevent the tissue from being damaged.

In detail, a cross-section of the lower body 411 parallel with the second direction X has a rounded rectangular shape and tapers toward the bottom center region 411a of the lower body 411.

Here, the bottom center region 411a of the lower body may be formed as a surface having a narrow width along the second direction X, or may be formed as a line.

As shown in FIG. 2 and FIG. 4, the press member 420 is bent and extended from one end of the contact member 410, and the height of the press member 420 gradually increases along the second direction X.

A first end of the press member 420 is smaller in height than a second end opposite to the first end. Here, the first end of the press member 420 refers to an end of the press member near to the stapling shaft 10.

Thus, the height of the stabilizer unit 400 in this embodiment gradually increases along the second direction X. Referring to FIG. 4, 'S1' is smaller than 'S2'.

The height of the contact member 410 is constant along the second direction X, so that a part of the contact member 410 discharged from the staple cartridge 100 has a constant discharging height.

Referring to FIG. 2, FIG. 3, FIG. 5 and FIG. 6, the pusher unit 200 includes a first pusher 210 for pressing the staples loaded into the first staple discharge hole array 130 in the first direction Z, and a second pusher 220 for pressing the staples loaded into the second staple discharge hole array 140 in the first direction Z.

The first pusher 210 includes a plurality of first unit pushers arranged at regular intervals in the second direction X, and the second pusher 220 includes a plurality of second unit pushers arranged at regular intervals in the second direction.

Referring to (a) of FIG. 5, the first pusher 210 includes a 1-1 pusher 211 for pushing 1-1 staples loaded into the 1-1 staple discharge hole line 131, a 1-2 pusher 213 for pushing 1-2 staples loaded into the 1-2 staple discharge hole line 132, a first pusher connector 214 for connecting the 1-1 pusher 211 and the 1-2 pusher 213, and a first pusher presser 212 to be pressed by the driving wedge 300.

The 1-1 pusher 211 includes a 1-1 body presser 211b to press a body of the 1-1 staple, and 1-1 leg pressers 211a protruding from opposite sides of the 1-1 body presser 211b to press legs of the 1-1 staple.

The 1-2 pusher 213 includes a 1-2 body presser 213b to press a body of the 1-2 staple, and 1-2 leg pressers 213a protruding from opposite sides of the 1-2 body presser 213b to press legs of the 1-2 staple.

A bottom of the 1-1 body presser 211b and a bottom of the 1-2 body presser 213b have to be flat to respectively press the body of the 1-1 staple and the body of the 1-1 staple.

Further, the 1-1 leg presser 211a and the 1-2 leg presser 213a are inserted in staple setting grooves (not shown) formed in the cartridge main body 110 and press the 1-1 staple and the 1-2 staple, respectively.

The 1-1 pusher 211 and the 1-2 pusher 213 are formed as a single body by the first pusher connector 214, and asymmetrically formed with respect to a center line of the first pusher 210 parallel with the second direction X.

Referring to (b) of FIG. 5, the second pusher 220 includes a 2-1 pusher 221 and a 2-3 pusher 223 symmetrically arranged with respect to a center line of the second pusher 220 parallel with the second direction X, and a 2-2 pusher 222 extended toward front ends of the 2-1 pusher 221 and the 2-3 pusher 223, i.e. in the second direction and formed in a center region with respect to a widthwise direction of the second pusher 220.

The 2-1 pusher 221, the 2-2 pusher 222 and the 2-3 pusher 223 are moved by external force to press the 2-1 staple, the 2-2 staple and the 2-3 staple loaded into the 2-1 staple discharge hole line 141, the 2-2 staple discharge hole line 142 and the 2-3 staple discharge hole line 143, respectively.

The 2-1 pusher 221, the 2-2 pusher 222 and the 2-3 pusher 223 have substantially the same shape as the 1-2 pusher 213, and thus repetitive descriptions thereof will be avoided.

Here, the length of the unit pusher in the second direction X is smaller than the length of the unit stabilizer. That is, the length of the unit stabilizer of the stabilizer unit in the second direction X is larger than the length of the unit pusher corresponding to the unit staple discharge hole.

Further, the height H2 of the stabilizer unit 400 in the first direction is greater than the height H1 of the pusher unit 200. Therefore, a first discharge height H4 of the stabilizer unit 400 discharged from the staple cartridge is higher than a second discharge height H3 of the pusher unit 200 discharged from the staple cartridge 100.

The second discharge height H3 approximates 0.1~1 mm, and the first discharge height H4 approximates 0.12~1.25 mm. Alternatively, the first discharge height and the second discharge height may be equal to each other.

Tissue is directly placed in between the stabilizer unit 400 and the anvil 600, but the staple is interposed in between the pusher unit 200 and the anvil 600. Therefore, the first discharge height H4 has to be higher than the second discharge height H3 by the thickness of the staple in order to stably hold the tissue between the anvil 600 and the staple cartridge 100. In this state, the tissue is not torn but safely cut by the blade.

Referring to FIG. 2 and FIG. 6, the driving wedge 300 includes a wedge body 310, a first wedge 320, a second wedge 330, a third wedge 340, a fourth wedge 350 and a guide wedge 360.

The first wedge 320 protrudes downward from and is extended from the wedge body 310, and is moved by external force to press the first pusher 210.

The second wedge 330 is arranged neighboring on the first wedge 320. The second wedge 330 protrudes downward from and is extended from the wedge body 310, and presses the stabilizer unit 400.

The guide wedge 360 is extended downward from a center region of the wedge body 310, and moves in the second direction X along the slit formed inside the cartridge main body 110.

The third wedge 340 and the fourth wedge 350 protrude downward from and are extended from the wedge body 310. The third wedge 340 and the fourth wedge 350 are formed at the side opposite to the first wedge 320 and the second wedge 330 with respect to the guide wedge 360. Here, the third wedge 340 and the fourth wedge 350 presses the second pusher 220.

In this embodiment, the protruding height of the first wedge 320 in the first direction Z is equal to the protruding height of the second wedge 330, but not limited thereto. Alternatively, the protruding height of the second wedge 330 may be greater than the protruding height of the first wedge 320. Further, the wedges may be separated from one another and formed independently of each other.

If the stabilizer unit 400 and the pusher unit 200 have the same height with each other, the protruding height of the second wedge 330 is greater than the protruding height of the first wedge 320 so that the first discharge height H4 of the stabilizer unit 400 discharged from the staple cartridge 100 can be greater than the second discharge height H3 of the pusher unit 200 discharged from the staple cartridge 100.

In the end effector of the surgical linear stapler according to this embodiment, the staple cartridge assembly is placed above the anvil. In other words, the anvil is placed below the staple cartridge assembly, but not limited thereto. Alternatively, the end effector of the surgical linear stapler according to this embodiment may have a structure where the anvil is placed above the staple cartridge assembly. That is, the staple cartridge assembly may be placed below the anvil.

Below, an end effector of a surgical linear stapler according to a second embodiment of the present invention will be described with reference to FIG. 8 to FIG. 10. In this embodiment, the end effector of the surgical linear stapler is substantially similar to the foregoing end effector of the surgical linear stapler according to the first embodiment of the present invention.

However, in the end effector of the surgical linear stapler according to the second embodiment on the contrary to the first embodiment, a stabilizer unit 1400 is provided as a single body elongated in the second direction without including the plurality of unit stabilizers, and provided on the cartridge main body 110.

Accordingly, the cartridge main body 110 includes a single stabilizer discharge slit 1150 elongated in the second direction between the first guide slit 120 and the first staple discharge hole array 130.

The stabilizer unit 1400 has substantially the same cross-section as the stabilizer unit according to the foregoing first embodiment. Specifically, the stabilizer unit 1400 includes a contact member 1410 and a press member 1420. The contact member 1410 includes an upper body 1413 and a lower body 1411. The lower body 1411 has a rounded surface gently formed toward a bottom center region thereof in order to prevent tissue from being damaged.

In this embodiment, the height of the stabilizer unit 1400 gradually increases in the second direction X. Referring to FIG. 10, S3 is smaller than S4.

Since the stabilizer unit 1400 is provided as a single member elongated in the second direction X, it is possible to hold tissue placed in between the staple cartridge 100 and the anvil 600 at once.

Below, an end effector of a surgical linear stapler according to a third embodiment of the present invention will be described with reference to FIG. 11 to FIG. 15. The end effector of the surgical linear stapler according to this exemplary embodiment is substantially similar to the foregoing end effector of the surgical linear stapler according to the first embodiment.

However, in the end effector of the surgical linear stapler according to the third embodiment, a stabilizer unit 2400 is placed on the staple cartridge 100 and includes a first stabilizer 2410 and a second stabilizer 2420 arranged at opposite sides with respect to the first guide slit 120.

The first stabilizer 2410 includes a plurality of first unit stabilizers, and the second stabilizer 2420 includes a plurality of first unit stabilizers. Further, the first unit stabilizer has the same shape as the second stabilizer.

The first unit stabilizer includes a contact member 2411 to be in contact with tissue, and a press member 2413 extended from one side of the contact member 2411 and pressed by the driving wedge 300.

The contact member 2411 includes an upper body 2411b extended from the press member 2413, and a lower body 2411a extended from the upper body 2411b and discharged from the staple cartridge 100 to directly contact the tissue.

The lower body 2411a has a rounded surface gently formed toward a bottom center region thereof in order to prevent the tissue from being damaged.

The press member 2413 protrudes from a lateral side of the contact member 2411, and the height of the press member 2413 gradually increases along the second direction X.

Although the height of the press member 2413 gradually increases along the second direction X, the height of the first unit stabilizer is constant along the second direction X since the press member 2413 protrudes from the lateral side of the contact member 2411 and the height of the contact member 2411 is constant along the second direction X.

In addition, the cartridge main body 110 includes a first staple discharge hole array 1130 and a second staple discharge hole array 1140, which are formed at opposite sides with respect to the first guide slit 120, a first stabilizer discharge slit 1161 formed between the first staple discharge hole array 1130 and the first guide slit 120 and allowing at least a part of the first stabilizer 2410 to be discharged, and a second stabilizer discharge slit 1163 formed between the second staple discharge hole array 1140 and the first guide slit 120 and allowing at least a part of the second stabilizer 2420 to be discharged.

Further, a pusher unit 1200 includes a first pusher 1210 for pressing the staples loaded into the first staple discharge hole array 1130 in the first direction Z, and a second pusher 1220 for pressing the staples loaded into the second staple discharge hole array 1140 in the first direction Z. Here, the first pusher 1210 and the second pusher 1220 have the same shape with each other, and is equivalent to the first pusher 210 as shown in (a) of FIG. 5. Thus, repetitive descriptions thereof will be avoided.

In FIG. 14, (a) shows a state before the stabilizer unit and the pusher unit are pressed by the driving wedge 300, and (b) shows a state that the stabilizer unit and the pusher unit are being pressed by the driving wedge 300.

In FIG. 15, (a) shows a state before tissue is stapled by the staples, and (b) shows a state that the tissue is stapled and then cut by the blade 510.

In the state that the first stabilizer 2410 and the second stabilizer 2420 are placed inside the cartridge main body 110 and the staples are respectively loaded into the first staple discharge hole array 1130 and the second staple discharge hole array 1140, if the first pusher 1210, the second pusher 1220, the first stabilizer 2410 and the second stabilizer 2420 are pressed by the driving wedge 300, stapling lines of two rows are formed at regular intervals in tissue at each side with respect to the cutting section A1 of the tissue as shown in (b) of FIG. 15.

Specifically, as shown in (a) of FIG. 15, the surgical site A of tissue arranged on the cartridge main body 110 is cut by the blade 510 into two surgical sites with respect to a virtual cutting line A0. One of the two surgical sites is a first surgical site C, and the other one is a second surgical site B to be remained in a human body.

If the end effector of the surgical linear stapler according to this embodiment starts operating, as shown in (b) of FIG. 15 the first surgical site C has stapling lines of two rows parallel with a cutting section A1, and the second surgical site B has stapling lines of two rows parallel with the cutting section A1.

Here, the distance D1 between a first stapling line 1aa, which is the nearest to the cutting section A1, of the stapling lines in the first surgical site C and the cutting section A1 is equal to the distance D1 between a second stapling line 3aa, which is the nearest to the cutting section A1, of the stapling lines in the second surgical site B and the cutting section A1.

Since both the first stapling line 1aa and the second stapling line 3aa are positioned more than a predetermined distance from the cutting section, tissue to be removed, i.e., biological tissue placed in between the cutting section A1 and the first stapling line 1aa in the first surgical site C is suitable for the tissue for pathological examination since it is not damaged at all.

Below, an end effector of a surgical linear stapler according to a fourth embodiment of the present invention will be described with reference to FIG. 16 to FIG. 18. The end effector of the surgical linear stapler according to the fourth embodiment is substantially similar to the foregoing end effector of the surgical linear stapler according to the third embodiment.

However, in the end effector of the surgical linear stapler according to the fourth embodiment on the contrary to the third embodiment, each of a first stabilizer 3410 and a second stabilizer 3420 is formed as a single body elongated in the second direction and provided on the cartridge main body 110 instead of including a plurality of unit stabilizers.

Accordingly, the cartridge main body 110 also includes a single first stabilizer discharge slit 1171 elongated in the second direction X between the first guide slit 120 and the first staple discharge hole array 1130, and another single second stabilizer discharge slit 1173 elongated in the second direction X between the first guide slit 120 and the second staple discharge hole array 1140.

Each cross-section of the first stabilizer 3410 and the second stabilizer 3420 has substantially the same shape as that of the first unit stabilizer provided in the stabilizer unit according to the foregoing third embodiment, and thus repetitive descriptions thereof will be avoided.

Below, an end effector of a surgical linear stapler according to a fifth embodiment of the present invention will be described with reference to FIG. 19 to FIG. 21. The end effector of the surgical linear stapler according to the fifth embodiment is substantially similar to the foregoing end effector of the surgical linear stapler according to the first embodiment.

However, in the end effector of the surgical linear stapler according to the fifth embodiment on the contrary to the first embodiment, the length of the unit stabilizer of the stabilizer unit in the lengthwise direction of the cartridge main body 110, i.e. in the second direction, the length of the unit pusher of the pusher unit, the length of the unit staple discharge hole of the first staple discharge hole array 2130, and the length of the unit staple discharge hole of the second staple discharge hole array 2140 are substantially the same with one another.

Specifically, a stabilizer unit 4400 includes a plurality of unit stabilizers arranged at regular intervals along the second direction X, and the pusher unit 200 includes a plurality of unit pushers arrange at regular intervals along the second direction X.

The first staple discharge hole array 2130 includes a plurality of first unit staple discharge holes, and the stabilizer discharge slit 1180 includes a plurality of unit discharge slits along the second direction X. The length of the unit stabilizer in the second direction X is substantially equal to the length of the unit pusher in the second direction X, and the length of the first unit staple discharge hole in the second direction X is substantially equal to the length of the unit discharge slit in the second direction X.

Here, the pusher unit 200 is substantially the same as the pusher unit according to the first embodiment, and thus repetitive descriptions thereof will be avoided. The unit stabilizer includes a contact member 4410, and a press member 4420. The contact member 4410 includes an upper body 44137 and a lower body 4411. The lower body 4411 has a rounded surface 4411b gently formed toward a bottom center region 4411a thereof in order to prevent the tissue from being damaged.

In addition, the anvil 600 according to this embodiment includes an anvil body 610, and the anvil body 610 includes a second guide slit 620 for guiding the blade 510 to move, and a first anvil groove array 630 and a second anvil groove array 640 which are formed at opposite sides with respect to the second guide slit 620.

Specifically, the first anvil groove array 630 includes a 1-1 anvil groove line 631 the most adjacent to the second guide slit 620, and a 1-2 anvil groove line 633 arranged at a predetermined distance from the 1-1 anvil groove line 631.

The 1-1 anvil groove line 631 includes a plurality of first unit anvil grooves formed at regular intervals on the cartridge main body 110 along the second direction X while forming one row.

Further, the second anvil groove array 640 includes a 2-1 anvil groove line 641 the most adjacent to the second guide slit 620, a 2-2 anvil groove line 642 arranged at a predetermined distance from the 2-1 anvil groove line 641, and a 2-3 anvil groove line 643 arranged at a predetermined distance from the 2-2 anvil groove line 642.

Here, a third distance between the 1-1 anvil groove line 631 and the second guide slit 620 is greater than a fourth distance between the 2-1 anvil groove line 641 and the second guide slit 620.

The 1-1 anvil groove line 631 corresponds to a 1-1 staple discharge hole line 2131, and the 2-1 anvil groove line 641 corresponds to a 2-1 staple discharge hole line 2141.

Therefore, as shown in (b) of FIG. 7, the distance D1 from the cutting section A1, where the tissue A is cut, to the first stapling line 1aa is greater than the distance D2 from the cutting section A1 to the second stapling line 3aa.

In result, the tissue between the cutting section A1 and the first stapling line 1aa is not damaged by the staples, and it is possible to obtain a tissue area for pathological examination, which is not damaged by the staples, from the tissue to be removed by the blade 510.

Further, the anvil body 610 includes a stabilizer corresponding surface 650 defined between the 1-1 anvil groove line 631 and the second guide slit 620.

The stabilizer corresponding surface 650 holds the tissue while facing a bottom of the stabilizer unit 4400.

Below, an end effector of a surgical linear stapler according to a sixth embodiment of the present invention will be described with reference to FIG. 22. The end effector of the surgical linear stapler according to the sixth embodiment is substantially similar to the foregoing end effector of the surgical linear stapler according to the fifth embodiment.

However, on the contrary to the fifth embodiment, the anvil body 610 in this embodiment includes a stabilizer corresponding projection 1650 protruding from a surface between the 1-1 anvil groove line 631 and the second guide slit 620 and facing the bottom of the stabilizer unit 4400 of FIG. 19.

Below, an end effector of a surgical linear stapler according to a seventh embodiment of the present invention will be described with reference to FIG. 23. The end effector of the surgical linear stapler according to the seventh embodiment is substantially similar to the foregoing end effector of the surgical linear stapler according to the fifth embodiment.

However, on the contrary to the fifth embodiment, the anvil body 610 in this embodiment includes a stabilizer corresponding groove 2650 recessed on a surface between the 1-1 anvil groove line 631 and the second guide slit 620 and facing the bottom of the stabilizer unit 4400 of FIG. 19.

Below, an end effector of a surgical linear stapler according to an eighth embodiment of the present invention will be described with reference to FIG. 24. The end effector of the surgical linear stapler according to the eighth embodiment is substantially similar to the foregoing end effector of the surgical linear stapler according to the fifth embodiment.

However, the anvil 600 provided in the end effector of the surgical linear stapler according to this embodiment includes the anvil body 610, and the anvil body 610 includes the second guide slit 620 for guiding the blade 510 to move, and a first anvil groove array 1630 and a second anvil groove array 1640 which are formed at opposite sides with respect to the second guide slit 620.

Further, the anvil body 610 includes a first surface 3651 formed between the first anvil groove array 1630 and the second guide slit 620 and holding tissue while facing a bottom of a first stabilizer 5410, and a second surface 3652 formed between the second anvil groove array 1640 and the second guide slit 620 and holding the tissue while facing a bottom of a second stabilizer 5420. Here, the first surface 3651 and the second surface 3652 are flat.

If the end effector of the surgical linear stapler in this embodiment starts operating, as shown in (b) of FIG. 15, a first surgical site C has stapling lines of two rows parallel with the cutting section A1, and a second surgical site B has stapling lines of two rows parallel with the cutting section A1.

The distance D1 between the first stapling line 1aa the nearest to the cutting section A1 between the stapling lines of the first surgical site C and the cutting section A1 is equal to the distance D1 between the second stapling line 3aa the nearest to the cutting section A1 between the stapling lines of the second surgical site B and the cutting section A1.

Here, both the first stapling line 1aa and the second stapling line 3aa are positioned more than a predetermined distance from the cutting section A1, so that tissue to be removed, i.e. biological tissue positioned from the cutting section A1 to the first stapling line 1aa within the first surgical site C can be suitable for the tissue for pathological examination since it is not damaged at all.

Below, an end effector of a surgical linear stapler according to a ninth embodiment of the present invention will be described with reference to FIG. 25. The end effector of the surgical linear stapler according to the ninth embodiment is substantially similar to the foregoing end effector of the surgical linear stapler according to the eighth embodiment.

However, on the contrary to the eighth embodiment, the anvil body 610 includes a first stabilizer corresponding projection 4651 protruding from a surface between the 1-1 anvil groove line 1631 and the second guide slit 620 and corresponding to the bottom of the first stabilizer 5410 (see FIG. 24), and a second stabilizer corresponding projection 4652 protruding from a surface between the 2-1 anvil groove line 1641 and the second guide slit 620 and corresponding to the bottom of the second stabilizer 5420 (see FIG. 24).

Below, an end effector of a surgical linear stapler according to a tenth embodiment of the present invention will be described with reference to FIG. 26. The end effector of the surgical linear stapler according to the tenth embodiment is substantially similar to the foregoing end effector of the surgical linear stapler according to the eighth embodiment.

However, on the contrary to the eighth embodiment, the anvil body 610 includes a first stabilizer corresponding groove 5651 protruding from a surface between the 1-1 anvil groove line 1631 and the second guide slit 620 and corresponding to the bottom of the first stabilizer 5410 (see FIG. 24), and a second stabilizer corresponding groove 5652 protruding from a surface between the 2-1 anvil groove line 1641 and the second guide slit 620 and corresponding to the bottom of the second stabilizer 5420 (see FIG. 24).

Below, an embodiment of a pusher-stabilizer unit capable of replacing the stabilizer unit and the pusher unit, which are used in the eighth embodiment, will be described with reference to FIG. 27.

In FIG. 27, (a) shows the pusher-stabilizer unit 700 obliquely viewed from, and (b) shows the pusher-stabilizer unit 700 viewed upside down from (a).

In this embodiment, the pusher-stabilizer unit 700 is achieved by forming the pusher unit and the stabilizer unit of the eighth embodiment as a single body. The pusher-stabilizer unit 700 is arranged at the right side with respect to the second guide slit 620 (see FIG. 24).

Specifically, the pusher-stabilizer unit 400 includes a pusher 710 and a stabilizer 720. The pusher is substantially the same as the pusher show in (a) of FIG. 5, and the stabilizer 720 is the same as the stabilizer unit of FIG. 21. Since the pusher 710 and the stabilizer 720 are integrated, they are simultaneously moved by the driving wedge in the height direction of the cartridge main body, i.e. in the first direction Z.

Below, another embodiment of a pusher-stabilizer unit capable of replacing the stabilizer unit and the pusher unit, which are used in the eighth embodiment, will be described with reference to FIG. 28.

In FIG. 28, (a) shows the stabilizer unit 7000 obliquely viewed from, and (b) shows the stabilizer unit 7000 viewed upside down from (a).

The pusher-stabilizer unit 7000 in this embodiment is analogous to the foregoing pusher-stabilizer unit. However, on the contrary to the foregoing pusher-stabilizer unit, the pusher-stabilizer unit in this embodiment includes a pusher 7100 and a stabilizer 7200 which are arranged in sequence along the lengthwise direction of the staple cartridge and formed as a single body. Here, the pusher-stabilizer unit 7000 is arranged at a left side with respect to the second guide slit 620 (see FIG. 24).

The end effector of the surgical linear stapler according to the present invention is as follows.

First, the stabilizer unit stably holds tissue between the cutting section of the tissue and the stapling line while being discharged from the staple cartridge when the staple cartridge and the anvil relatively move in order to staple the tissue, thereby having an advantage of stably cutting the tissue with the blade in the state that the tissue is not torn.

Second, the distance from the cutting section to the stapling line of an organ site to be removed is greater than the distance from the cutting section to the stapling line of the surgical site to be remained in a human body while cutting one organ into two areas and stapling them, thereby having an advantage of preventing the cutting margin of the biological tissue for the examination from being damaged within the surgical site to be removed. In result, it is possible to stably and conveniently obtain a tissue area for pathological examination, which is not damaged by a staple, in a surgical site of an organ to be removed.

Although a few exemplary embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. An end effector of a surgical linear stapler, comprising:
    a staple cartridge which is internally loaded with staples for stapling tissue;
    an anvil which corresponds to the staple cartridge and forms the staple discharged from the staple cartridge;
    an upper cover placed over the staple cartridge;
    a pusher unit which is arranged within the staple cartridge while corresponding to the staple and pushes the staple in a first direction defining a height direction of the staple cartridge while being moved by external force so that the staple can be discharged from the staple cartridge;
    a driving wedge which is arranged within the staple cartridge and presses the pusher unit in the first direction while being moving along a second direction defining a lengthwise direction of the staple cartridge by external force;
    a stabilizer unit which is arranged within the staple cartridge while being disposed adjacent to the pusher unit and at least partially discharged from the staple cartridge in the first direction while being moved by the driving wedge,
    wherein the stabilizer unit is configured to contact tissue after pressed by the driving wedge so that the tissue is placed between the stabilizer unit and the anvil without being stapled by the staple;
    an indicator provided on an outer surface of the upper cover corresponding to a position of the stabilizer unit; and
    a blade unit which comprises a blade for cutting the tissue stapled by the staples and moves the driving wedge in the second direction,
    wherein the staple cartridge comprises a cartridge main body, and the cartridge main body comprises a first guide slit for guiding the blade to move, a first staple discharge hole array and a second staple discharge hole array formed at opposite sides with respect to the first guide slit, and a stabilizer discharge slit formed in between the first staple discharge hole array and the first guide slit and allowing the stabilizer unit to be at least partially discharged, wherein the indicator indicates a position where the stabilizer unit is arranged with respect to the first guide slit on the staple cartridge.

2. The end effector of the surgical linear stapler according to claim 1, wherein the stabilizer unit comprises a contact member to be in contact with tissue, and a press member extended from one side of the contact member and pressed by the driving wedge, and the contact member comprises a lower body to be in direct contact with the tissue, the lower body comprising a rounded surface formed gently toward a bottom center region of the lower body to prevent the tissue from being damaged.

3. The end effector of the surgical linear stapler according to claim 2, wherein a second cross-section parallel with the second direction among cross-sections of the lower body comprises a rounded rectangular shape, and tapers toward the bottom center region of the lower body.

4. The end effector of the surgical linear stapler according to claim 2, wherein the contact member is constant in height along the second direction, and the press member is gradually increased in height along the second direction.

5. The end effector of the surgical linear stapler according to claim 2, wherein the press member is bent and extended from one end of the contact member, and the stabilizer unit is gradually increased in height along the second direction.

6. The end effector of the surgical linear stapler according to claim 2, wherein the press member protrudes from a lateral side of the contact member, and the stabilizer unit is constant in height along the second direction.

7. The end effector of the surgical linear stapler according to claim 1, wherein the pusher unit and the stabilizer unit are formed as a single body and simultaneously moved in the first direction by the driving wedge.

8. The end effector of the surgical linear stapler according to claim 1, wherein a first distance between a first innermost staple discharge hole line of the first staple discharge hole array, which is the most adjacent to the first guide slit line, and the first guide slit is greater than a second distance between a second innermost staple discharge hole line of the second staple discharge hole array, which is the most adjacent to the first guide slit, and the first guide slit, in order to obtain tissue for pathological examination, which is not damaged by the staples, from tissue to be cut by the blade and removed.

9. The end effector of the surgical linear stapler according to claim 1, wherein the staple cartridge comprises a cartridge main body, and the cartridge main body is formed with a first guide slit for guiding the blade to move, and the stabilizer unit is arranged on the staple cartridge and comprises a first stabilizer and a second stabilizer arranged at opposite sides with respect to the first guide slit.

10. The end effector of the surgical linear stapler according to claim 9, wherein the cartridge main body comprises a first staple discharge hole array and a second staple discharge hole array, which are formed at opposite sides with respect to the first guide slit, a first stabilizer discharge slit formed in between the first staple discharge hole array and the first guide slit and allowing the first stabilizer to be at least partially discharged, and a second stabilizer discharge slit formed in between the second staple discharge hole array and the first guide slit and allowing the second stabilizer to be at least partially discharged.

11. The end effector of the surgical linear stapler according to claim 9, wherein the anvil comprises an anvil body, the anvil body comprising a second guide slit for guiding the blade to move, and a first anvil groove array and a second anvil groove array which are formed at opposite sides with respect to the second guide slit, and the anvil body comprises a first surface formed in between the first anvil groove array and the second guide slit and holing the tissue while facing a bottom of the first stabilizer, and a second surface formed in between the second anvil groove array and the second guide slit and holing the tissue while facing a bottom of the second stabilizer.

12. The end effector of the surgical linear stapler according to claim 1, wherein the stabilizer unit comprises a plurality of unit stabilizers arranged at regular intervals along the second direction, and the pusher unit comprises a plurality of unit pushers arranged at regular intervals along the second direction, and the unit stabilizer is longer in the second direction than the unit pusher.

13. The end effector of the surgical linear stapler according to claim 12, wherein the first staple discharge hole array comprises a plurality of first staple discharge hole lines arranged at regular intervals along a third direction defining a widthwise direction of the staple cartridge, and each of the first staple discharge hole lines comprises a plurality of first unit staple discharge holes arranged at regular intervals along the second direction, the stabilizer discharge slit comprises a plurality of unit discharge slits formed at regular intervals along the second direction, and the unit discharge slit is longer in the second direction than the first unit staple discharge hole.

14. The end effector of the surgical linear stapler according to claim 1, wherein the stabilizer unit comprises a plurality of unit stabilizers arranged at regular intervals along the second direction, and the pusher unit comprises a plurality of unit pushers arranged at regular intervals along the second direction, the first staple discharge hole array comprises a plurality of first unit staple discharge holes, and the stabilizer discharge slit comprises a plurality of unit discharge slits along the second direction, and the unit stabilizer has the same length in the second direction as the unit pusher, and the first unit staple discharge hole has the same length in the second direction as the unit discharge slit.

15. The end effector of the surgical linear stapler according to claim 1, wherein the driving wedge comprises a first wedge pressing the pusher unit, and a second wedge arranged neighboring on the first wedge and pressing the stabilizer unit, and a protruding height of the second wedge in the first direction is greater than a protruding height of the first wedge so that a first discharge height of the stabilizer unit discharged from the staple cartridge can be greater than a second discharge height of the pusher unit discharged from the staple cartridge.

16. The end effector of the surgical linear stapler according to claim 1, wherein the stabilizer unit is higher in the first direction than the pusher unit so that a first discharge height of the stabilizer unit discharged from the staple cartridge can be greater than a second discharge height of the pusher unit discharged from the staple cartridge.

17. The end effector of the surgical linear stapler according to claim 1, wherein the anvil comprises an anvil body, the anvil body comprising a second guide slit for guiding the blade to move, and a first anvil groove array and a second anvil groove array which are formed at opposite sides with respect to the second guide slit, and a third distance between a first anvil groove line of the first anvil groove array, which is the most adjacent to the second guide slit, and the second guide slit is greater than a fourth distance between a second anvil groove line of the second anvil groove array, which is the most adjacent to the second guide slit, and the second guide slit.

18. The end effector of the surgical linear stapler according to claim 17, wherein the anvil body comprises a stabilizer corresponding surface defined in between the first anvil groove line and the second guide slit, the stabilizer corresponding surface holds the tissue while facing a bottom of the stabilizer unit, and the stabilizer corresponding surface is flat.

19. The end effector of the surgical linear stapler according to claim 17, wherein the anvil body comprises a stabilizer corresponding groove recessed on a surface between the first anvil groove line and the second guide slit and corresponding to a bottom of the stabilizer, or a stabilizer corresponding projection protruding from the surface and corresponding to the bottom of the stabilizer.

\* \* \* \* \*